United States Patent
Hume et al.

(10) Patent No.: US 9,403,893 B2
(45) Date of Patent: Aug. 2, 2016

(54) AVIAN COLONY STIMULATING FACTOR 1 RECEPTOR BINDING PROTEINS

(75) Inventors: David Arthur Hume, Roslin (GB); Dave Burt, Roslin (GB); David Sester, Roslin (GB); Valerie Garceau, Roslin (GB); Jacqueline Smith, Roslin (GB); Bob Paton, Roslin (GB)

(73) Assignee: The University Court of the University of Edinburgh, Edinburgh (GB)

( * ) Notice: Subject to any disclaimer, the term of this patent is extended or adjusted under 35 U.S.C. 154(b) by 0 days.

(21) Appl. No.: 13/380,185

(22) PCT Filed: Jun. 22, 2010

(86) PCT No.: PCT/GB2010/001221
§ 371 (c)(1),
(2), (4) Date: Mar. 12, 2012

(87) PCT Pub. No.: WO2010/149960
PCT Pub. Date: Dec. 29, 2010

(65) Prior Publication Data
US 2012/0183495 A1    Jul. 19, 2012

(51) Int. Cl.
*C07K 14/53* (2006.01)
*A61K 38/19* (2006.01)
*C12N 15/27* (2006.01)
*C12N 15/09* (2006.01)
*C12N 15/63* (2006.01)
*C12N 1/21* (2006.01)
*C07K 14/54* (2006.01)
*A61K 38/00* (2006.01)

(52) U.S. Cl.
CPC .............. *C07K 14/53* (2013.01); *A61K 38/193* (2013.01); *C07K 14/54* (2013.01); *C12N 15/09* (2013.01); *C12N 15/63* (2013.01); *A61K 38/00* (2013.01)

(58) Field of Classification Search
None
See application file for complete search history.

(56) References Cited

U.S. PATENT DOCUMENTS

2009/0317403 A1    12/2009    Aharinejad et al.

FOREIGN PATENT DOCUMENTS

WO    WO 01/30381 A2    5/2001

OTHER PUBLICATIONS

Eck, S. L. and Wilson, J. M.,1996, in: Goodman & Gilman's The Pharmacological Basis of Therapeutics, Ninth Edition, McGraw-Hill, New York.*
Ladner et al., EMBO J., 1987, vol. 6(9):2693-2698.*
Garceau V et al. Pivotal advance: avian colony-stimulating factor 1 (CSF-1), interleukin-34 (IL-34), and CSF-1 receptor genes and gene products. Journal of Leukocyte Biology. May 2010; 87: 753-764.
Database EMBL (Online). Gallus gallus finished cDNA, clone chEST591h11. Feb. 2, 2004. Abstract. 1 page.
Hamilton JA et al. Particulate adjuvants can induce macrophage survival, DNA synthesis, and a synergistic proliferative response to GM-CSF and CSF-1. Journal of Leukocyte Biology. Feb. 2000; 67(2): 226-232.
Lin H et al. Discovery of a cytokine and its receptor by functional screening of the extracellular proteome, Science. May 9, 2008; 320(5877): 807-811.
Gibson MS et al. Identification of chicken granulocyte colony-stimulating factor (G-CSF/CSF3): the previously described myelomonocytic growth factor is actually CSF3. Journal of Inteferon & Cytokine Research. Jun. 1, 2009; 29(6): 339-343.
Stiglec R et al. Frequency of cancer genes on the chicken Z chromosome and its human homologues: implications for sex chromosome evolution. Comparative and Functional Genomics. vol. 2007; Article ID 43070, 8 pages, (2007).
International Search Report and Written Opinion, PCT/GB2010/001221, mailed Oct. 1, 2010.

* cited by examiner

*Primary Examiner* — Xiaozhen Xie
(74) *Attorney, Agent, or Firm* — Myers Bigel & Sibley, P.A.

(57) ABSTRACT

The present invention provides avian CSF1 genes encoding proteins which bind avian colony stimulating factor 1 receptor (CSF1R) and which exhibit immunomodulatory properties Chicken CSF1          Chicken SCF Chicken IL34    Chicken CSF1    Chicken SCF Chicken IL34

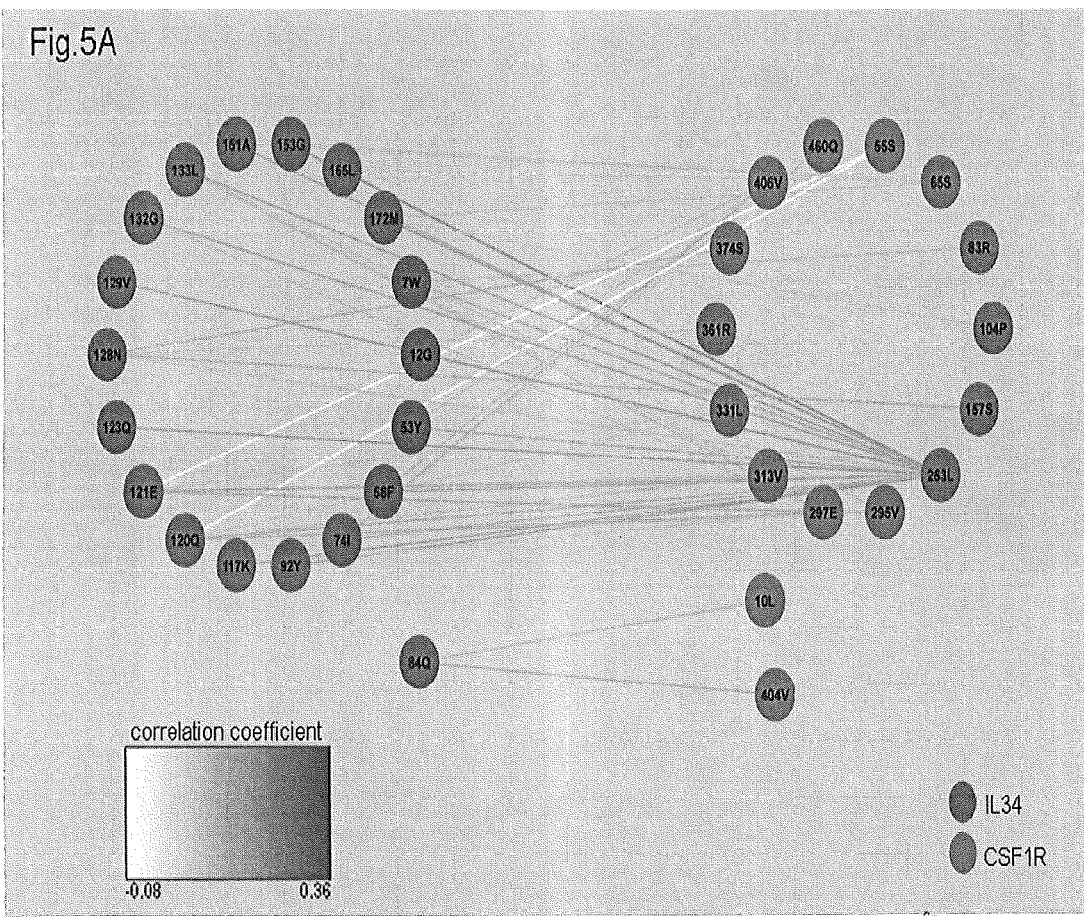

AVIAN COLONY STIMULATING FACTOR 1 RECEPTOR BINDING PROTEINS

RELATED APPLICATIONS

Figure 1A:
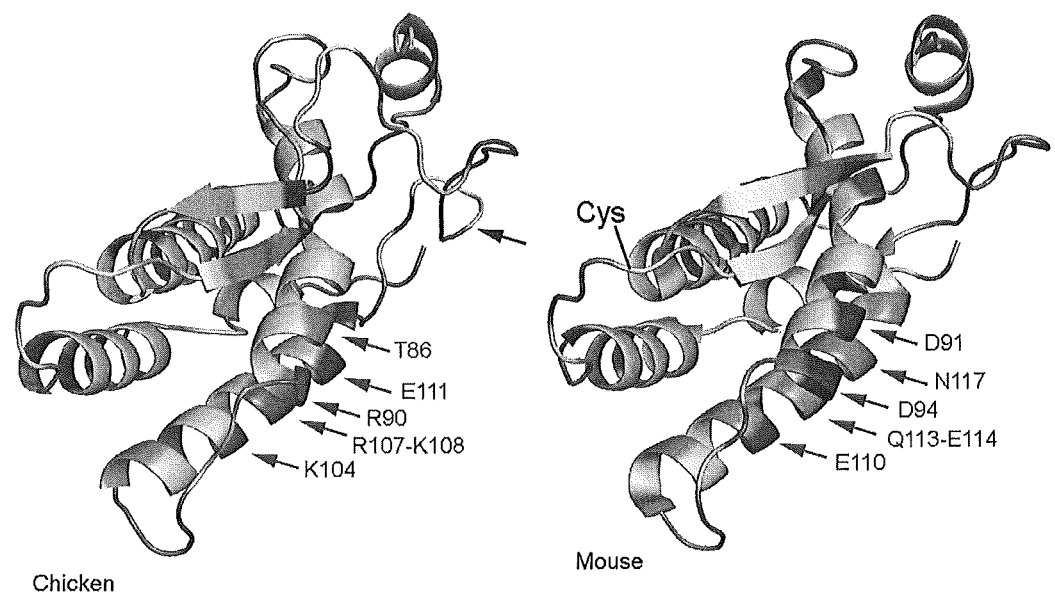

This application is a 35 U.S.C. 0371 national phase entry of PCT Application PCT/GB2010/001221, filed Jun. 22, 2010, and published in English on Dec. 29, 2010, as International Publication No. WO 2010/149960, and which claims the priority to United Kingdom Application No. 0910833.3, filed Jun. 23, 2009, the disclosure of each of which is incorporated herein by reference in its entirety.

FIELD OF THE INVENTION

The present invention relates to newly identified avian genes which encode proteins which bind avian colony stimulating factor 1 receptor (CSF1R). Through binding to CSF1R, these proteins exhibit immunomodulatory properties which may be exploited to modulate the avian immune system as well as effects on cell growth, differentiation and/or proliferation, organ/tissue development and vaccine efficacy.

BACKGROUND OF THE INVENTION

Mononuclear phagocytes are derived from progenitor cells in the bone marrow which differentiate into blood monocytes and then enter the tissues to occupy specific niches (Hume et al. 2002). They constitute the first line of defense against pathogens, maintain homeostasis, and have trophic functions ranging from bone morphogenesis to neuronal patterning in sexual development, from angiogenesis to adipogenesis (Pollard 2009). Macrophage colony-stimulating factor (CSF1) is required for normal differentiation, proliferation and survival of macrophage lineage cells (Sweet and Flume 2003; Chitu and Stanley 2006; Bonifer and Hume 2008). Mice and rats bearing mutations in the CSF1 gene (i.e. op/op mice and tl/tl rats) show a mononuclear phagocyte deficiency, and their important developmental abnormalities, such as reduced somatic growth, perinatal mortality, osteopetrosis, neurological and reproductive defects, highlight many of the macrophage trophic roles mentioned above (Marks et al. 1992; Pollard 1997, 2009; Ryan et al. 2001).

Although CSF-1 exists in a number of isoforms, most biochemical studies have focused on the minimal biologically active fragment i.e. the 154 N-terminal amino acids, common to all isoforms. In a full-length CSF1 molecule, this receptor-binding region is preceded by a 32-amino-acid signal peptide, and followed by a variable spacer region, a 24-amino-acid transmembrane region and a 35-amino-acid cytoplasmic tail. The tertiary structure of the active fragment of CSF1 forms a short-chain four-helical bundle (A, B, C and D) with small regions of beta-sheet (1 and 2). The helices are paired into A-C and B-D by intrachain disulfide bonds, while one interchain disulfide bond generates a mature homodimer with a two-fold rotation axis (Pandit et al. 1992). The crystal structure of mouse CSF1 bound to its receptor, CSF1R, was recently solved to a resolution of 2.4 Å, showing that CSF1 N-terminal segment (residues 6-15), helix B (residues 55-66) and helix C (residues 79-85) are implicated in receptor binding. (PDB code 3EJJ) (Chen et al. 2008).

All CSF1 effects are mediated through binding to the CSF1 receptor (CSF1R), a glycoprotein of 165 kDa that is encoded by the c-fms proto-oncogene (Dai et al. 2002). CSF1R is a member of the type III protein tyrosine kinase family, along with PDGFRA, PDGFRB and c-kit, and shares with other family members a characteristic extracellular region of five immunoglobulin-like domains (D1 to D5), a single transmembrane helix and a intracellular tyrosine kinase domain (Rosnet and Birnbaum 1993). CSF-1 associates tightly with the receptor ($K_D$=0.4 nM at 37° C.) in a 2:2 stoichiometry (Guilbert and Stanley 1986). This binding involves the CD loop (residues 141-151) and the EF loop (residues 168-173) of D2, as well as the BC and DE loops (residues 231-232 and 250-257 respectively) of D3 (Chen et al. 2008).

The expression of CSF1R on the cell surface is amongst the earliest events in macrophage lineage commitment, and is mostly restricted to these cells throughout embryonic development as well as in adults (Lichanska et al. 1999) Like other myeloid promoters, the proximal CSF1R promoter lacks the classic TATA box and GC-rich sequences but contains recognition sites for AML1 transcription factors, and for transcription factors of the C/EBP and Ets families, including the myeloid-restricted transcription factor PU.1 (Reddy et al. 1994; Himes et al. 2005; Bonifer and Hume 2008). Expression of CSF1R is also controlled by FIRE (Fms Intronic Regulatory Element) a highly-conserved enhancer element in the first intron (Nimes et al. 2001; Sasmono et al. 2003).

Most of the phenotypic defects seen in the op/op mice including reproductive defects and perturbations in organ development, are even more severe in the CSF1R knockout mice (Dai et al. 2002). First attributed to the availability of maternal-derived CSF1, these observations can now be explained by the recent discovery of a second ligand for the human CSF1R, designated IL34, with an activity on monocyte viability. IL34 was purified as a homodimer composed of 241-amino acid monomers, and shown to be expressed mostly in the brain but also in many other tissues including heart, spleen, lung, liver, kidney and thymus (Lin et al. 2008).

WO2008/031172 describes the use of CSF1 to promote organ development in warm-blooded animals and in particular premature human foetuses/embryos. Furthermore, WO03028752 describes methods and compositions for modulating immune responses in animals, said methods comprising modulating CSF1 activity.

The chicken has been used widely in studies of early embryonic myelopoiesis (Lichanska et al. 1999; Lichanska and Hume 2000), but compared to our knowledge of the mammalian mononuclear phagocyte system, our knowledge of avian systems is rather limited and neither WO2008/031172 or WO03028752 describe the existence of an avian CSF1 gene. Indeed, there are only two characterized colony-stimulating factors in chickens. Chicken GM-CSF (CSF2) has been cloned and shown to drive the proliferation of chicken bone marrow cells (Avery et al. 2004). The other described chicken CSF, myelomonocytic growth factor, has recently been shown to be the chicken ortholog of G-CSF (CSF3) (Gibson et al. 2009). Apparent orthologs of the GM-CSF receptor alpha chain, and the beta chain, shared with the IL3 receptor, are annotated in the chicken genome (Ensembl). So far, no function for the CSF1R has been demonstrated in birds, CSF1 was believed to be absent from avian genomes and IL34 had not been recognized (Kaiser 2007).

CSF1 and IL34 in humans were reported to have little obvious homology, and in mammals at least, CSF1 has evolved rather rapidly. The existence of two ligands for a single receptor is difficult to maintain across evolution if they evolve independently of each other and of the receptor.

SUMMARY OF THE INVENTION

The present invention concerns the identification of novel avian genes encoding proteins which bind avian colony stimulating factor 1 receptor (CSF1R). In particular, the invention describes, for the first time, the existence of avian genes encoding colony stimulating factor 1 (CSF1) and interleukin 34 (IL34). It should be noted that these findings contradict the statement by Kaiser (2007) that there is no CSF1 equivalent present in the avian genome.

Furthermore, the inventors have surprisingly discovered that the avian CSF1R is expressed by macrophages—this is in contrast to other species, for example fish, where the CSF1R is expressed in other cell types.

In view of the avian CSF1R expression profile, the inventors have discovered that through binding to CSF1R, avian CSF1 and IL34 exhibit immunomodulatory properties which may be exploited to modulate the avian immune system as well as effects on cell growth, differentiation and/or proliferation, organ/tissue development and vaccine efficacy.

It should be understood that references to the terms "avian" or "avian species" should be taken to encompass all species within the Class, Aves and in particular those species classified as belonging to the Order, Galliformes and/or the Genus, *Gallus*. Avian species now known to harbour CSF1 and IL34 genes may include, for example, *Gallus gallus* otherwise known as the domestic chicken and/or other poultry or fowl species. In other embodiments, the term "avian" may be construed as including species classified within the Order, Passeriformes, such as, for example, finches, in particular, the zebra finch. In general, the terms "avian CSF1 gene", "avian IL34 gene", "avian IL34 protein" and "avian CSF1 protein" encompass CSF1 and/or IL34 genes, proteins (and fragments thereof) present in, or encoded by, the genomes of the avian species described herein.

The inventors have ascertained the sequences of certain avian forms of CSF1 and the cDNA sequence of an exemplary CSF1 gene, present in the *Gallus gallus* genome, is given below as SEQ ID NO: 1:

SEQ ID NO: 1

```
ATAAAGGGCAGCGCGGCGGCGACGGCGGACTCAGCCCGGCCCCGCTCCGCCGCCTTCTCCCGCACCGCCC

GACCCGCCGCAGCCCCGGCCCCACGGCAGCCCCCATGCCCCGCCTCGGATCCCAGGTGTCCCTGTTCCGC

TGCACCCTGCTCTCGTCCCTCCTCCTCGTCTGCAGCATCCATGAGACGGAGCAGAACAGCTACTGCCAGC

AGATCATCACCGAGCGGCACCTGGACCACCTGCAGGAGCTGGCGGACACGCAGATGCAGCAGCCGGGCAC

AGTGTCCTTCAGATTCATCAGCAAGATGCGGCTGAGCGACTCTGTCTGCTACGTGAAAGCCGCCTTCCCT

TTGCTGGGCACCATCCTGAACAGGACGACGTTCAAGGAGAACTCAACAAACGCCAACAAGATGAAGACGG

TGCGCAAGATGTACGAAAACATCGATGAGAACGTGGACCCCTGCATCAGGGACGAGGATGACAAGGAGCA

CGCGCTGTCCGAAATGTGCTTTGAGGAGTTCACCACGTCCCCCTACGAGATGCTGGTGCTGGTGAGGCAG

TTCTTCGAGGACATCAAACAGCTGCTGCAGAACAAGGAGACCTTCGAGAAGGACTGCAGCCAGGTGTACC

GCAGTGCGTGCGCGGGGCCCCGGCAGCACAGCTCCTCCCCAGGTGTGGGGACAGATCCTGACTGCAATTG

CCTGTCCCCTGCCCTCCCTTCTGCCACCCAGCCCTCCCTCTCCGCTGCCACCCGTGCCGGCAGGGACGTG

GCGCCCGCTAGCACCAGGGTCCCTTACCGCCAGCTCGGTGGCATCCTGGCTGAGTTAGGCAGCAGTGCCC

CGTCCGAGCCCCCCAGTAGCGTGGAGGGCAGCTCGGGGGCCGAGGAACTGCCAGGAGCCGGGCTCGGCGA

CGCGTCGGCGCCGTCCCCCACCATGCAGCAGACGCTTGGAGCCCTCCTGGATCCAGCCGCGAGCGCCGGC

CCGAAGGCTGAGGACGTATCCATCCCGTCCCACGGGATGCCGGAGGAGGGCGCCGGGACCCCCGCCCTCC

CACATCGGCTCCCTTCGCCGCGAGGGATCAGCGCGGCGATGCCGGCGGCGGTCCCCAGCAGCGGCTCTGC

GCAGCGCCGCGGGGTCGGGCGCCGTCCCACCGAGAGCCCCGAGCGGGTCACGCAGCTCCGCTTCCCCAGG

ATGGCTCCGCCGTTGCGGGGCCGGGCGGAGGGCGGCCCCGGGGACGGGGCGAGGGCGCGAGGCTGGGGGC

TGAGCCGGCTGCGGGAGCCCGAGGACGGCGGGGCCGGACCCAGCTTTGATTCGAGCTTTGTTCTGAGCGC

AGAGCAGCGCAGGAAGGAGCCGCCAGCCGCCAGCGGGGGGCACCGGGAGCTCCTGGTGTACGTCACGGTG

GCCAGCGTGGTGGCCGTGCTGCTGGCCATGGGCGGGCTGCTCTTCTACAAGTATAAGTCCAAGGTCCTGC

AGCGGGGAGCAGCGCTAAAAGAGGGGGGCTGCGACCCCGAGGAGCCGGAGAGCAGGGCGCTGCAGGGAGC

GCAGGGCTGCGCGGAGCTGGAGACGCAGGAGCTGTGAGGGCCCCCTGCGGGACGTGATGCTGCTCGGGGG

GACGGACGGGGACGCTCCTCGCTGGGCGACGGACGGCTGCTGCTCGGCCTCCCCCCGCCGCGATGACCCC

CAGGCCCTGTCCTGCAGCTGCAACCCACGGGTGAGGATGGCAGGACGGGGCGGTGCAGCCCTGCAGGACC

CCGGCGATGGGGCGGATGGCACCGAGGGGCTCCACGGGGACGGCATTGGGTGCCGCGAGTGGAACATCTC

CCCCCACCCATCCACGGTTCCCGTTGCTCCTCTCCCACCCCTGGCACGGGGGGACCCCCGGCGCCCCATG
```

-continued

```
GGGGGACCCCTCCCGCATCCCACCGGTGCCGAGGACCCAACGCCCGGCCTGCAAAGGGGGAAACCCTCAC

ACTGTGAATATTTAAGACCCGTGGTGCCGTCCCCATCCCGCGATCCCAAGCTGGCCTTGGGAGCTGCCCG

GCGCCGCTCTGCGCAGGAAGGCTCTCCACGAACGCGGTGGATAAACGCTTTTATCCAACAAATGCACTTG

GGGGGGGGGGTTCCCCCCTCCCTGCAGGGTTATTGCTGCGAGCTGGCCTCGCCCCAGACTGGATTTTGTT

GCTGGAGCACAGCACGGCAATGGGGCCGTGGCTGCAGTGTGGGGTTTGGGGGCTCAGCGGTACCCGGACT

GCGTCCCACCCCACACGGCATCCCTGCCCAGCGCCGCTCCCGGGGGGTCGGAAGTGTTATTTTTATATTA

CATGAGATGCAAACGGGACGGAGCACATTGGGGTGTGGTGGGGTTTTGTTTTTTAAAGCATTAGTATTGA

TTTTGGGGTTTTTTTTTCTATGCGTATTTATGGACTGCCAAAAAAAGAGGCGTTTCCTGGGGGTGATGGG

GGGGGGGGTGGAAGTGGGGTGCAGAGCCGGGCTGGGGCCGGAGCTGGTGCTGGCTCAGTATGTGGGGTGT

GGGTGAGGGGGGTTGGGGGGGGGGCAGCTTTTGGAGCTCTTTCTGCCTCTGTTGTCTCATTTTTTGTACA

GTGAAATGGTGAAATATTTTATACAAAGTCATTTAAAGAAGTCTATTTAAGGAAAATAATAGAAAACAGC

TTGTATATTTAATATTATTAATAAAGATGGACGTGCAAAAAAAAAAAAAAA
```

The native CSF1 *Gallus gallus* sequence, comprises eight exons and yields two transcripts, one encoding a protein of 490 amino acids, the other a protein of 270 amino acids. The transcript encoding the longer, 490 amino acid protein is provided below as SEQ ID NO: 2

```
                                                                SEQ ID NO: 2
ATGCCCCGCCTCGGATCCCAGGTGTCCCTGTTCCGCTGCACCCTGCTCTCGTCCCTCCTCCTCGTCTGCA

GCATCCATGAGACGGAGCAGAACAGCTACTGCCAGCAGATCATCACCGAGCGGCACCTGGACCACCTGCA

GGAGCTGGCGGACACGCAGATGCAGCAGCCGGGCACAGTGTCCTTCAGATTCATCAGCAAGATGCGGCTG

AGCGACTCTGTCTGCTACGTGAAAGCCGCCTTCCCTTTGCTGGGCACCATCCTGAACAGGACGACGTTCA

AGGAGAACTCAACAAACGCCAACAAGATGAAGACGGTGCGCAAGATGTACGAAAACATCGATGAGAACGT

GGACCCCTGCATCAGGGACGAGGATGACAAGGAGCACGCGCTGTCCGAAATGTGCTTTGAGGAGTTCACC

ACGTCCCCTACGAGATGCTGGTGCTGGTGAGGCAGTTCTTCCAGGACATCAAACAGCTGCTGCAGAACA

AGGAGACCTTCGAGAAGGACTGCAGCCAGGTGTACCGCAGTGCGTGCGCGGGCCCCGGCAGCACAGCTC

CTCCCCAGGTGTGGGGACAGATCCTGACTGCAATTGCCTGTCCCCTGCCCTCCCTTCTGCCACCCAGCCC

TCCCTCTCCGCTGCCACCCGTGCCGGCAGGGACGTGGCGCCCGCTAGCACCAGGGTCCCTTACCGCCAGC

TCGGTGGCATCCTGGCTGAGTTAGGCAGCAGTGCCCCGTCCGAGCCCCCAGTAGCGTGGAGGGCAGCTC

GGGGGCCGAGGAACTGCCAGGAGCCGGGCTCGGCGACGCGTCGGCGCCGTCCCCACCATGCAGCAGACG

CTTGGAGCCCTCCTGGATCCAGCCGCGAGCGCCGGCCCGAAGGCTGAGGACGTATCCATCCCGTCCCACG

GGATGCCGGAGGAGGGCGCCGGGACCCCCGCCCTCCCACATCGGCTCCCTTCGCCGCGAGGGATCAGCGC

GGCGATGCCGGCGGCGGTCCCCAGCAGCGGCTCTGCGCAGCGCCGCGGGGTCGGGCGCCGTCCCACCGAG

AGCCCCGAGCGGGTCACGCAGCTCCGCTTCCCCAGGATGGCTCCGCCGTTGCGGGGCCGGGCGGAGGGCG

GCCCCGGGGACGGGGCGAGGGCGCGAGGCTGGGGCTGAGCCGGCTGCGGGAGCCCGAGGACGGCGGGGC

CGGACCCAGCTTTGATTCGAGCTTTGTTCTGAGCGCAGAGCAGCGCAGGAAGGAGCCGCCAGCCGCCAGC

GGGGGGCACCGGGAGCTCCTGGTGTACGTCACGGTGGCCAGCGTGGTGGCCGTGCTGCTGGCCATGGGCG

GGCTGCTCTTCTACAAGTATAAGTCCAAGGTCCTGCAGCGGGAGCAGCGCTAAAAGAGGGGGGCTGCGA

CCCCGAGGAGCCGGAGAGCAGGGCGCTGCAGGGAGCGCAGGGCTGCGCGGAGCTGGAGACGCAGGAGCTG

TGA
```

The inventors have ascertained that SEQ ID NO: 2 encodes the following amino acid sequence (given as SEQ ID NO: 3).

SEQ ID NO: 3
MPRLGSQVSLFRCTLLSSLLLVCSIHETEQNSYCQQIITERHLDHLQELADTQMQQPGTVSFRFISKMRL
SDSVCYVKAAFPLLGTILNRTTFKENSTNANKMKTVRKMYENIDENVDPCIRDEDDKEHALSEMCFEEFT
TSPYEMLVLVRQFFQDIKQLLQNKETFEKDCSQVYRSACAGPRQHSSSPGVGTDPDCNCLSPALPSATQP
SLSAATRAGRDVAPASTRVPYRQLGGILAELGSSAPSEPPSSVEGSSGAEELPGAGLGDASAPSPTMQQT
LGALLDPAASAGPKAEDVSIPSRGMPEEGAGTPALPHRLPSPRGISAAMPAAVPSSGSAQRRGVGRRPTE
SPERVTQLRFPRMAPPLRGRAEGGPGDGARARGWGLSRLREPEDGGAGPSEDSSFVLSAEQRRKEPPAAS
GGHRELLVYVTVASVVAVLLAMGGLLFYKYKSKVLQRGAALKEGGCDPEEPESRALQGAQGCAELETQEL

The second transcript encoding the shorter, 270 amino acid protein is given below as SEQ ID NO: 4:

SEQ ID NO: 4
ATGCCCCGCCTCGGATCCCAGGTGTCCCTGTTCCGCTGCACCCTGCTCTCGTCCCTCCTCCTCGTCTGCA
GCATCCATGAGACGGAGCAGAACAGCTACTGCCAGCAGATCATCACCGAGCGGCACCTGGACCACCTGCA
GGAGCTGGCGGACACGCAGATGCAGCAGCCGGGCACAGTGTGCTTCAGATTCATCAGCAAGATGCGGCTG
AGCGACTCTGTCTGCTACGTGAAAGCCGCCTTCCCTTTGCTGGGCACCATCCTGAACAGGACGACGTTCA
AGGAGAACTCAACAAACGCCAACAAGATGAAGACGGTGCGCAAGATGTACGAAAACATCGATGAGGACGT
GGACCCCTGCATCAGGGACGAGGATGACGAGGAGCACGCGCTGTCCGAAATGTGCTTTGAGGAGTTCACC
ACGTCCCCCTACGAGATGCTGGTGCTGGTGAGGCAGTTCTTCCAGGACATCAAACAGCTGCTGCAGAACA
AGGAGACCTTCGAGAAGGACTGCAGCCAGGTGTACCGCAGTGCGTGCGCGGGGCCCCGGCAGCACAGCTG
CTCCCCAGAGCAGCGCAGGAAGGAGCCGCCAGCCGCCAGCGGGGGGCACCGGGAGCTCGTGGTGTACGTC
ACGGTGGCCAGCGTGGTGGCCGTGCTGCTGGCCATGGGCGGGCTGCTCTTCTACAAGTATAAGTCCAAGG
TCCTGCAGCGGGGAGCAGCGCTAAAAGAGGGGGGCTGCGACCCCGAGGAGCCGGAGAGCAGGGCGCTGCA
GGGAGCGCAGGGCTGCGCGGAGCTGGAGACGCAGGAGCTGTGA

SEQ ID NO: 4 encodes the following amino acid sequence (given as SEQ ID NO: 5):

SEQ ID NO: 5
MPRLGSQVSLFRCTLLSSLLLVCSIHETEQNSYCQQIITERHLDHLQELADTQMQQEGTVSFRFISKMRL
SDSVCYVKAAFPLLGTILNRTTFKENSTNANKMKTVRKMYENIDEDVDPCIRDEDDEEHALSEMCFEEFT
TSRYEMLVLVRQFFQDIKQLLQNKETFEKDCSQVYRSACAGPRQHSSSPEQRRKEPPAASGGHRELLVYV
TVASVVAVLLAMGGLLFYKYKSKVLQRGAALKEGGCDPEEPESRALQGAQGCAELETQEL

In addition to the above, the inventors have ascertained the sequences of the avian IL34 gene and the sequence of an exemplary IL34 gene, present in the *Gallus gallus* genome, is given below as SEQ ID NO: 6:

SEQ ID NO: 6
ATGCACCAGGGCTGCGCGGCTGTCCTCTGTGTCCTGGCCGTGCTGGGGCTGGAGGTGGCTGCGCTGGGG
GAATGCGAGCTCGCCCGCCTGCTGCAGGACAAGCTGCGGTATGAGATGCGCCTGCAGTACATGAAGCAC
AACTTCCCCATTGACTACACTCTCCGGGTGCAGCACGAGGAGGTGCTGCGGACCGCCAACGTCACCCGC
CTGCGTGATGGGAAGGTGTCGGAGGCGTCGCTGCGCTACCTGTGGTTCCACGCCTGCTCCCAGGCGGTG
CTGCACATCCTCGAGGTGCTGCCGGAGAAGCACCCGTCCCGTGGGTACACGCAGGAGCTGAGCCAGCTT

-continued

```
TTGGATGCCCTGGGCGTGGAGTACAGTGGGTACCGGCAGAGCGATGTGGACGCGGTGGTGGCCGACCTG

GTGAAGCAGCTGCACAGCGGCGATAGCCGGCAGAAGGCCGTGCGCCCCAAAGCACTGCTGGACAACTGC

CTCAAGGTCCTGCGGATGCTCTTCGGGGCACACTGTCGGTGGGACTCCGCT
```

SEQ ID NO: 6 encodes the following amino acid sequence (given as SEQ ID NO: 7):

SEQ ID NO: 7

```
MHQGCAAVLCVLAVLGLEVAALGECELARLLQDKLRYEMRLQYMKHNFPIDYTLRVQHEEVLRTANVTR

LRDGKVSEASLRYLWFHACSQAVLHILEVLPEKHPSRGYTQELSQLLDALGVEYSGYRQSDVDAVVADL

VKQLHSGDSRQKAVRPKALLDNCLKVLRMLFGAHCRWDSA
```

As such, in a first aspect, the present invention relates to the sequences designated SEQ ID NOS: 1-7, encoding avian CSF1 genes (SEQ ID NOS: 1, 2 and 4), the avian IL34 gene (SEQ ID NO: 6), avian CSF1 proteins (SEQ ID NOS: 3 and 5) and the avian IL34 protein (SEQ ID NO: 7). In a further embodiment, the present invention provides fragments, analogues, portions, mutants, variants, derivatives and/or homologues/orthologues of any of the sequences described herein. Advantageously, the fragments, analogues, portions, mutants, variants, derivatives and/or homologues/orthologues provided by this invention might be functional or active—that is, they retain the function of the wild type avian CSF1 and IL34 genes/proteins.

The term "mutants" may encompass naturally occurring nucleic acid or protein mutants or those artificially created by the introduction of one or more nucleic acid or amino acid additions, deletions, substitutions or inversions.

Sequences homologous to the avian CSF1 and IL34 nucleic acid/protein sequences detailed above may be found in a number of different avian species, including each of those species belonging to the various Classes and Orders described above. One of skill will appreciate that homologous sequences may exhibit as little as approximately 20 or 30% sequence homology or identity however, in other cases, homologous sequences may exhibit at least 40, 50, 60, 65 70, 75, 80, 85, 90, 91, 92, 93, 94, 95, 96, 97, 98, 99% homology or identity to the various sequences given above. As such, homologous forms of other avian species are to be included within the scope of this invention.

Using the various nucleic acid and amino acid sequences described herein, one of skill in the art could readily identify related sequences in other avian species. For example, nucleic acid obtained from a particular species may be probed using the fragments or portions of the sequences described herein, for homologous or closely related sequences. In other methods, antibodies specific to or selective for the CSF1 or IL34 proteins described herein may be used to probe for or bind homologous proteins in other avian species. Such antibodies are described in more detail below.

Natural variations due to, for example, polymorphisms, may exist between the sequences of CSF1 and IL34 genes or proteins isolated from any given species; these variants may manifest as proteins and/or genes which exhibit one or more amino acid/nucleic acid substitutions, additions, deletions and/or inversions relative to a reference sequence (for example any of the sequences described above). It is to be understood that all such variants, especially those which are functional and/or display the desired activity, are to be included within the scope of this invention.

Additionally, or alternatively, analogues of the various amino acid sequences (i.e. proteins or peptides) described herein may be made by introducing one or more conservative amino acid substitutions into the primary sequence. One of skill in this field will understand that the term "conservative substitution" is intended to embrace the act of replacing one or more amino acids of a protein or peptide with an alternate amino acid with similar properties and which does not substantially alter the physio-chemical properties and/or structure or function of the native (or wild type) protein. Analogues of this type are also encompassed with the scope of this invention.

As is well known in the art, the degeneracy of the genetic code permits substitution of one or more bases in a codon without changing the primary amino acid sequence. Consequently, although the sequences described in this application are known to encode avian CSF1 and IL34 proteins, the degeneracy of the code may be exploited to yield variant nucleic acid sequences which encode the same primary amino acid sequences.

The provision of certain avian CSF1 and IL34 gene and/or protein sequences renders it possible for one skilled in this field to express and/or purify avian CSF1 and IL34 genes and/or proteins. By way of example, standard laboratory techniques may be used to express and/or purify recombinant avian CSF1 and IL34 genes and/or proteins. In one embodiment, the CSF1 and IL34 nucleic acid sequences described herein (or indeed any fragments or portions thereof) may be introduced into vector systems which can, inturn, be introduced into prokaryotic and/or eukaryotic cells for expression—such vectors may be known as eukaryotic/prokaryotic expression vectors. The methods and vectors which may be used in such techniques are described in detail by Sambrook et al., (Molecular Cloning: A Laboratory Manual, CSHL, 1989). By way of example, the avian CSF1 and IL34 genes (or fragments thereof) described herein may be cloned into a variety of vectors including, for example, plasmids, bacteriophages, cosmids, viral vectors, yeast artificial chromosomes and/or bacterial artificial chromosomes.

CSF1 and IL34 genes and/or proteins can be expressed with or without a fused heterologous sequence. CSF1 or IL34 fusion proteins may be generated and expressed using pET and pGEX type vectors which comprise short nucleic acid sequences encoding heterologous peptide sequences, such as, for example, peptide tags, immediately downstream of the cloning site. Vectors of this type are particularly useful for generating tagged CSF1 and IL34 proteins which can easily be removed, isolated or purified from heterogeneous protein mixtures by, for example, affinity purification procedures.

Suitable methods for isolating tagged (fusion) proteins, such as, for example, those tagged or fused to short peptides comprising, for example histidine or glutathione s-transferase moieties, include the use of nickel columns or glutathione-sephaprose substrates. Other techniques are detailed in Sambrook et al., (1989).

Vectors into which CSF1 or IL34 genes (or fragments thereof) have been cloned, may be introduced or transfected into cells using a variety of techniques—such techniques may otherwise be referred to as transfection protocols. Transfection protocols utilise conditions which render cell membranes permeable to compounds such as nucleic acids. By way of example, it may be possible to facilitate the transfection of vectors, including expression vectors, into cells using electroporation, heat shock, chemical compounds such, for example, calcium phosphate, stronitium phosphate, microinjection techniques and/or gene guns.

As such, in a second aspect, the present invention provides a vector comprising an avian CSF1 and/or IL34 gene or a fragment thereof. In one embodiment, the vector may be an expression vector containing elements for driving expression in a host cell.

In a third aspect, the invention provides a cell transfected with a vector according to this invention. By way of example, the host cell may be a prokaryotic or a eukaryotic cell such as, for example a bacterial cell such as one selected from the group consisting of *E. coli, Pseudomonas* sp. and *Bacillus* sp. or, in another embodiment, a yeast, fungal, insect, plant or animal cell.

In certain embodiments, the fused or unfused recombinant avian CSF1 and/or IL34 proteins provided by this invention may be used to generate antibodies which exhibit an affinity for, or are specific to, or selective for, a recombinant avian CSF1/IL34 or a fragment thereof. In particular, the recombinant avian CSF1 and IL34 proteins may be used to immunise animals (for example rodents and the like) to generate polyclonal sera, or with hybridomas to generate monoclonal antibodies. As such, a fourth aspect of this invention provides binding agents, for example antibodies, that bind specifically (or selectively) to one or more epitopes present in an avian CSF1 or IL34 protein, such as, for example, those described herein.

The avian CSF1/IL34 genes/proteins described herein may be exploited to execute a variety of immunological effects in the avian host. For example, methods or compounds which modulate avian CSF1/IL34 gene expression and/or protein levels may be used to modulate avian cell, for example monocyte/macrophage, production, proliferation, survival and/or differentiation. In addition, methods or compounds which modulate avian CSF1/IL34 gene expression and/or protein levels may be used to modulate the growth, proliferation and/or survival of tissues and/or organs.

Modulation of CSF1/IL34 genes/proteins may result in modulation of mature avian macrophage/monocyte function. In particular, avian macrophage phagocytic and our tumoricidal activity may be enhanced by the methods or compounds described herein.

In other embodiments, methods or compositions which modulate avian CSF1/IL34 gene/protein expression/levels may be used to regulate primary avian immune responses and/or prime immune system cells for subsequent activation stimuli. By way of example, the production of cytokines, for example, pro-inflammatory cytokines, may be modulated by the methods (uses which exploit the avian CSF1/IL34 genes/proteins described herein or compounds which modulate the expression or levels of CSF1/IL34 genes/proteins.

In view of the above, a fifth aspect of this invention provides a method of modulating avian growth and/or organ development, said method comprising the step of modulating the expression of the avian CSF1 or IL34 genes and/or the level of CSF1 or Il34 protein.

In a sixth aspect, the present invention provides the use of an avian CSF1 or IL34 gene and/or protein for modulating avian growth and/or organ development.

In mammalian systems, the production of circulating monocytes and tissue macrophages from the bone marrow is dependent upon the activity of CSF1 and IL34. The discovery that the avian genome also encodes CSF1 and IL34 genes, provides a means by which avian monocyte/macrophage development may be modulated.

As such, in a seventh aspect, the present invention provides a method of modulating the avian immune system, said method comprising the step of modulating the expression of the avian CSF1 and/or IL34 genes and/or the level of the CSF1 and/or IL34 proteins.

In an eighth aspect, the present invention provides the use of an avian CSF1 and/or IL34 gene and/or avian CSF1 and/or IL34 protein for modulating the avian immune system.

One of skill in this field will appreciate that by increasing the level of avian CSF1 or IL34 gene expression, it may be possible to increase macrophage development. Similarly, by increasing the in vivo level of CSF1 or IL34, it may be possible to modulate monocyte/macrophage development.

Commercial and domestic farming is reliant on effective vaccines to ensure avian stocks, for example poultry/fowl species, remain healthy while farmed. It is well established that the efficacy of a vaccine can be enhanced or improved with the use of an adjuvant. Adjuvants which can be used in combination with vaccines for use in farming are particularly useful and in this regard, avian CSF1 and IL34 proteins, for example the *Gallus gallus* CSF1 and IL34 proteins (or fragments thereof) described herein, may be used as vaccine adjuvants. As such, a ninth aspect of this invention provides avian CSF1 and IL34 proteins, or fragments thereof, for use as vaccine adjuvants.

In a tenth aspect, the present invention provides immunogenic compositions, potentially useful as avian vaccines, said immunogenic compositions comprising an avian CSF1 and/or IL34 protein.

The ability of CSF1 or IL34 proteins to promote the development of myeloid cells provides a further use for the avian CSF1 and/or IL34 proteins described herein as agents which can be used to induce or promote the growth of macrophages and/or other myeloid cells in vitro. By using avian CSF1 or IL34 proteins to facilitate the generation of populations of myeloid cells, it may be possible to produce populations of myeloid cells for use in research.

One of skill will appreciate that levels of gene expression can be modulated by administering one or more copies of the gene to a subject. By way of example, copies of the avian CSF1 and/or IL34 genes (or functional fragments thereof) may be administered to an avian subject in the form of an expressible vector such as those described above. In other embodiments, purified avian CSF1 and/or IL34 proteins (perhaps a recombinant avian CSF1 or IL34 proteins) may be administered to avians to increase the amount of circulating CSF1 and/or IL34. In one embodiment, an avian CSF1 or IL34 protein or gene (or functional fragment thereof) may be added or administered directly to a particular cell type, tissue or organ. For example, an avian CSF1 or IL34 protein or gene may be administered directly to avian bone marrow.

It should be understood that the terms "modulate" or "modulating" refer to an increase or decrease in the level of CSF1 or IL34 gene expression and/or CSF1 or IL34 protein levels, relative to, for example, the level of expression or protein observed in a normal, healthy (wild-type) avian subject. In one embodiment, the level of CSF1 or IL34 gene expression or levels of CSF1 or IL34 protein, may be modulated in vivo.

In other embodiments, compounds which modulate the expression of the avian CSF1 and/or IL34 genes and/or level of CSF1/IL34 proteins may be used to achieve any of the effects detailed above or in any of the described methods. Such compounds may include, for example, small organic molecules, nucleic acids (including sense and antisense DNA/RNA sequences) and antibodies and/or antigen binding fragments thereof. In one embodiment, compounds capable of inhibiting lactoferrin concentration and/or expression may include, for example, DNA or RNA oligonucleotides, preferably antisense oligonucleotides. Oligonucleotides useful as modulators of avian CSF1/IL34 gene and/or protein expression may be RNA molecules known to those skilled in this field as small/short interfering and/or silencing RNA and which will be referred to hereinafter as siRNA. Such siRNA oligonucleotides may take the form of native RNA duplexes or duplexes which have been modified in some way (for example by chemical modification) to be nuclease resistant. Additionally, or alternatively, the siRNA oligonucleotides may take the form of short hairpin RNA (shRNA) expression or plasmid constructs.

The skilled man will readily understand that antisense oligonucleotides may be used to modulate (for example, inhibit, down-regulate or substantially ablate) the expression of any given gene. Accordingly, (antisense) oligonucleotides provided by this invention may be designed to modulate, i.e. inhibit or neutralise, the expression and/or function of avian CSF1/IL34 genes and/or the protein products thereof.

By analysing native or wild-type lactoferrin sequences and with the aid of algorithms such as BIOPREDsi, one of skill in the art could easily determine or computationally predict nucleic acid sequences that have an optimal knockdown effect for these genes. Accordingly, the skilled man may generate and test an array or library of different oligonucleotides to determine whether or not they are capable of modulating the expression or function of avian CSF1/IL34 lactoferrin genes and/or proteins.

The identification of genes which bind the avian CSF1R to bring about increased myeloid cell production, proliferation and/or differentiation, may be exploited in methods for screening avians for individuals which exhibit increased levels of CSF1 and/or IL34 gene expression or increased levels of CSF1 and/or IL34 protein. Avians with these phenotypes may be particularly useful in, for example, breeding programs.

As such, an eleventh aspect the present invention provides a method of screening avian species, particularly agriculturally significant or important avian species (such as, for example, those classified as poultry or fowl) for potential inclusion in breeding programs said method comprising the steps of:

a) providing a nucleic acid sample from an avian species; and
b) comparing the level of expression of the CSF1 and/or IL34 gene(s) with a reference nucleic acid sample or value;

wherein avian species which exhibit and increased level of CSF1 and/or IL34 gene expression relative to a that present in a reference nucleic acid sample or value, may be selected for inclusion in breeding programs.

In one embodiment, the reference nucleic acid sample may be derived from an avian individual which exhibits normal or wild type CSF1/IL34 gene expression. In other embodiments, the reference nucleic acid value may represent the mean, average or median level of avian CSF1/IL34 gene expression.

In a twelfth aspect, the present invention provides a compound capable of inhibiting CSF1/IL34 gene expression or protein production for treating conditions, such as inflammatory diseases, resulting from or associated with aberrant CSF1/IL34 gene/protein expression. The present invention may also extend to uses of such compounds for the manufacture of medicaments and methods of treating avian diseases resulting from or associated with aberrant CSF1/IL34 gene/protein expression. The term "compounds" may include small organic molecules, fragments of native avian CSF1/IL34 proteins, CSF1/IL34 binding agents (for example antibodies or antigen binding fragments thereof) or nucleic acids, for example antisense sequences designed to inhibit the expression of avian CSF1/IL34 genes.

DETAILED DESCRIPTION

The present invention will now be described in more detail with reference to the following Figures which show:

FIG. 1: Structure-based sequence analysis of chicken CSF1. A. Ribbons representation of the chicken (left) and mouse (right) CSF1 structures. The PDB file for the chicken CSF1 was generated using 3D-Jigsaw with the mouse CSF1 structure as template (PDB 3ejj). The figures were rendered by PyMol in Polyview-3D. Residues are colored according to hydrophilicity where yellow is used for hydrophobic residues (A, C, F, G, I, L, M, P, V), dark yellow for amphipathic residues (H, W, Y), orange for polar residues (N, Q, S, T), red for residues charged negatively (D, E) and brown for residues charged positively (R, K). The cysteine forming the interchain disulfide bond is labelled on the mouse structure. The loop created by the presence of additional amino acids in the chicken sequence is marked by a black arrow. The red arrows show non-conserved substitutions within the binding site 1 to CSF1R as described in the mouse (Chen et al. 2008). B. Dimer interface of chicken CSF1 (left) and SCF (right). Residues are colored as in A. Amino acids present at the homodimer interface are highlighted by rendering their atoms as spheres.

FIG. 2: Structure-based sequence analysis of the chicken IL34. A. Ribbons representation of the chicken IL34 (left). Structures of the chicken CSF1 (center) and chicken SCF (right) are shown for comparison. The PDB file for the chicken IL34 was generated using 3D-Jigsaw with the mouse CSF1 structure as template (PDB 3ejj). The PDB file for the chicken SCF was generated using 3D-Jigsaw with the human SCF structure as template (PDB 1exz). The figures were rendered by PyMol in Polyview-3D. Residues are colored as in FIG. 1A. The red arrows highlight the corresponding residues composing the receptor binding site 1 in CSF1. B. Dimer interface of chicken IL34. Residues are colored as in A. Amino acids present at the homodimer interface are highlighted by rendering their atoms as spheres.

FIG. 3: Characterization of the avian CSF1R. A. Ribbons representation of CSF1-binding site 1 of the zebra finch (left) and chicken (right) CSF1R. The PDB files for the chicken and zebra finch CSF1R were created with 3D-Jigsaw using the mouse CSF1R structure as template (PDB 3ejj). The figures were rendered by PyMol in Polyview-3D. Residues are colored as in FIG. 1A. Arrows point at some of the non-conserved amino acid substitutions. B. Superimposition of the zebra finch (left) and chicken (right) D1-D3 domains of CSF1R with their respective CSF1 ligand. The two CSF1R structures are viewed from the same angle as in FIG. 3A. The chicken CSF1 structure from FIG. 1A is here rendered as surface in Polyview-3D. The PDB file for the zebra finch CSF1 structure was created with 3D-Jigsaw using the mouse CSF1 as template (PDB 3ejj) and rendered with Polyview-3D. Residues are colored as in FIG. 1A. C. Pustell DNA matrix alignment of the 5' ends of the avian CSF1R genes. The two genes align up to 2.5 kb upstream and through the first intron. D. Sequence alignment of the promoter-exon 1 region of the zebra finch and chicken CSF1R gene. Alignment was performed using MacVector. Binding sites for PU.1, C/EBP and AML1 are identified. E. Alignment of the highly-conserved segment in the intron of the zebra finch and chicken CSF1R gene. Alignment was performed as in D. Binding sites for PU.1, C/EBP and AML1 are identified. F. Localization of CSF1R mRNA in chick embryo at 20HH by whole mount In Situ. The figure shows the antisense (left) and the sense control ISH (right).

Figure 4A:
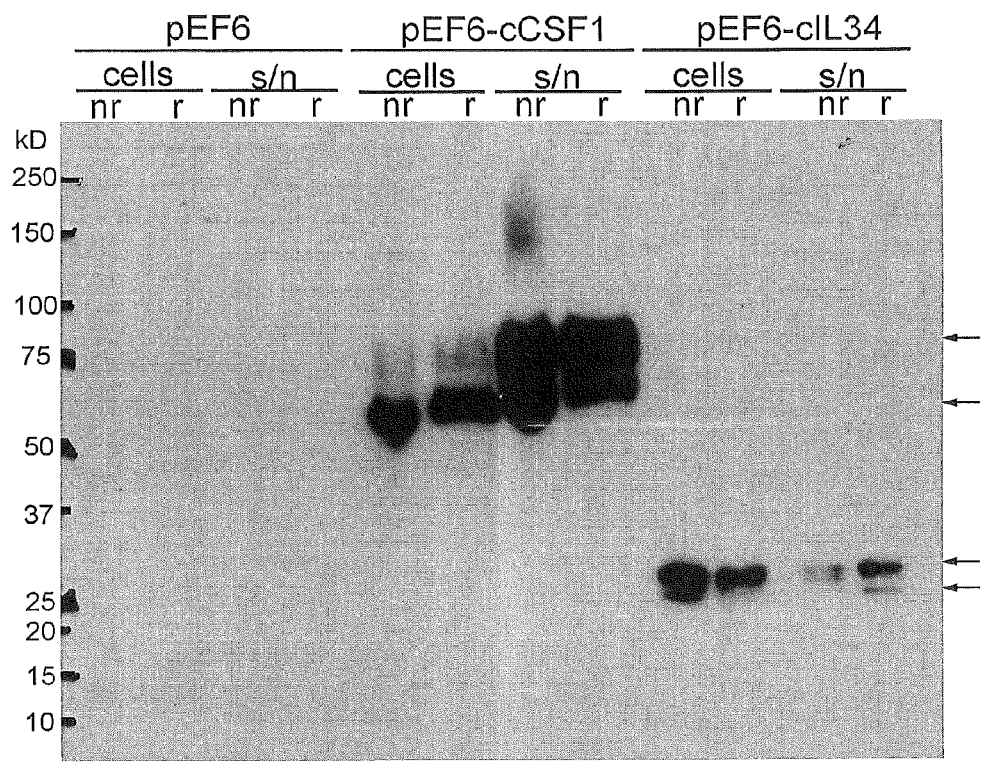
Figure 4B:
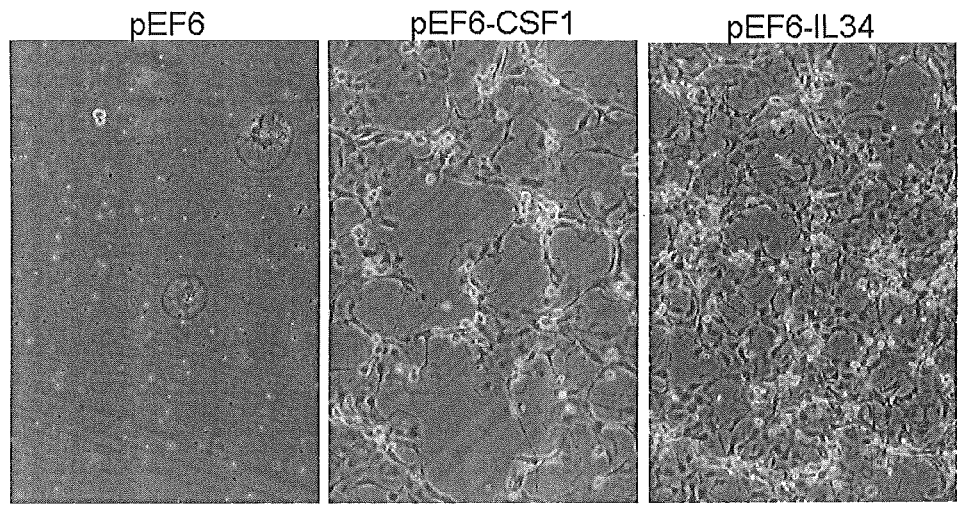

FIG. 4: Expression and activity of the chicken CSF1 and IL34. A Expression and secretion of chicken CSF1 and IL34 by HEK293T transfected with pEF6-cCSF1, pEF6-cIL34 or empty pEF6 vector. The cells were transfected using Lipofectamine and incubated for 72 hours. The cell lysates and supernatants were run on SDS-page gel in non-reducing and reducing conditions, and probed with an anti-V5 tag antibody. The arrows show the double bands for the chicken CSF1 (ca. 60 kD) and IL34 (ca. 25 kDa) in which the upper bands are the glycosylated forms of these proteins, whereas the lower bands constitute de non-glycosylated forms. B Chicken bone marrow derived macrophages at Day 10 of differentiation using 20% supernatant from pEF6 (left), pEF6-cCSF1 (centre) and pEF6-cIL34 (right) transfected HEK293T.

FIG. 5: Co-evolution of CSF1, IL34 and CSF1R. A. Diagram summarizing the main results of the co-evolution analyses performed by CAPS, a PERL-based software (Fares and McNally 2006a). The co-evolving residues between IL34 (left, in pink) and CSF1R extracellular domain (right, in blue) are shown as identified by CAPS (Fares and McNally 2006a). The correlation coefficient is indicated by the color of the line between two coevolving amino acids, and measures the correlated evolutionary variation at these sites. The residue numbers refer to the human sequences. B. Speculated IL34 binding mode of CSF1R based on the co-evolution analysis. The ribbons representation of the chicken CSF1R D1-D5 was created by superimposing the chicken CSF1R D1-D3 model produced for FIG. 3 and a chicken CSF1R D4-D5 model made using the human KIT D1-D5 (PDB 2e9w) as template in 3D-Jigsaw. The chicken IL34 model is the same as in FIG. 2 in a slightly different angle. All the models were rendered in Polyview-3D. The residues are colored as in FIG. 1A with the co-evolving homologous residues in chicken highlighted in blue.

Figure 6:
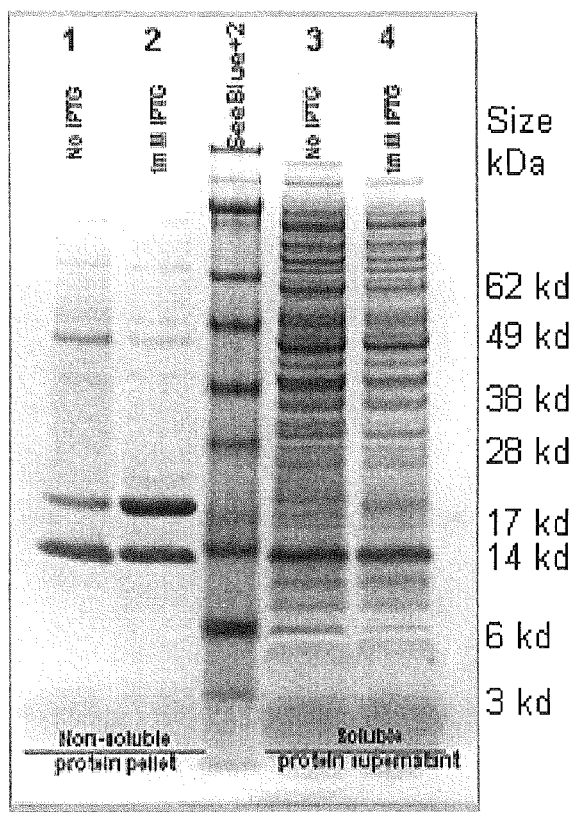

FIG. 6: Bis-Tris NuPAGE analysis of IPTG induced protein expression

Figure 7:
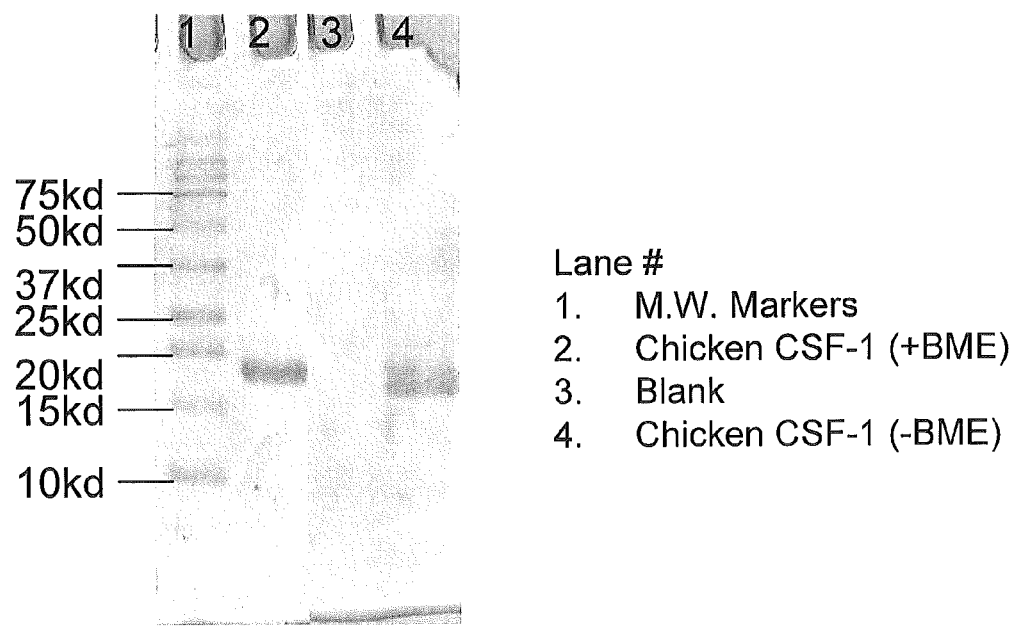

FIG. 7: SDS-PAGE analysis of the concentrated monomeric chicken CSF-1 protein

Figure 8:
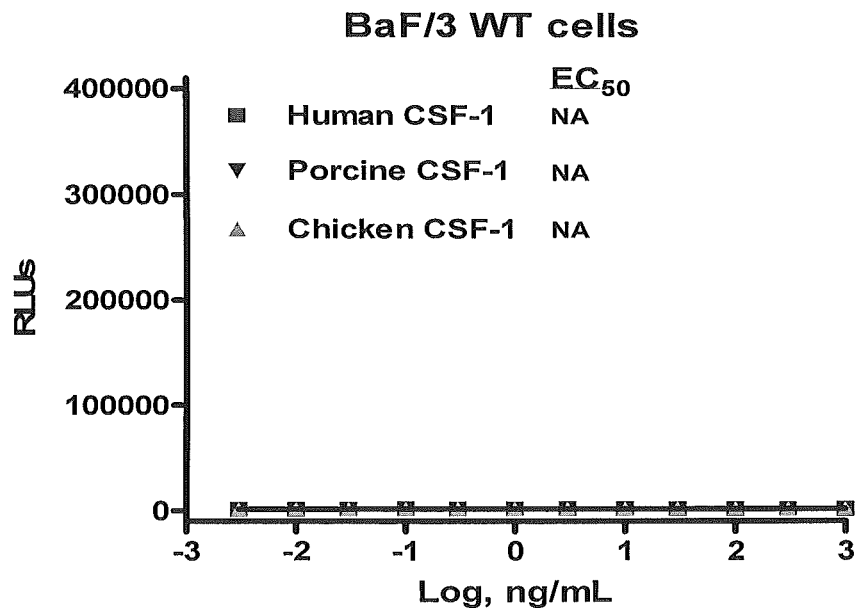

FIG. 8: Dose-Reponses data for all three CSF1 preparation on the parental BaF/3 cell line.

Figure 9:
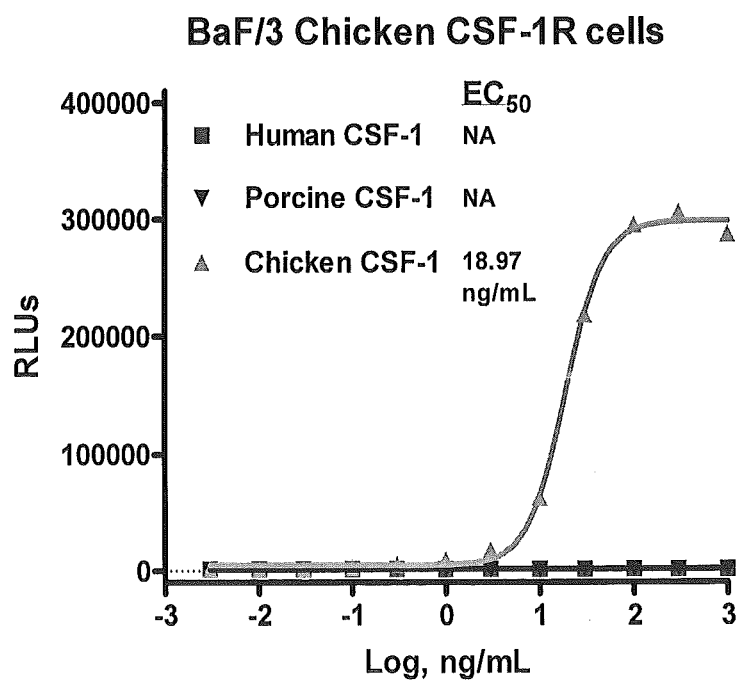

FIG. 9: Dose-Reponses data for all three CSF1 preparation on chicken CSF1R-expressing BaF/3 cells.

Figure 10:
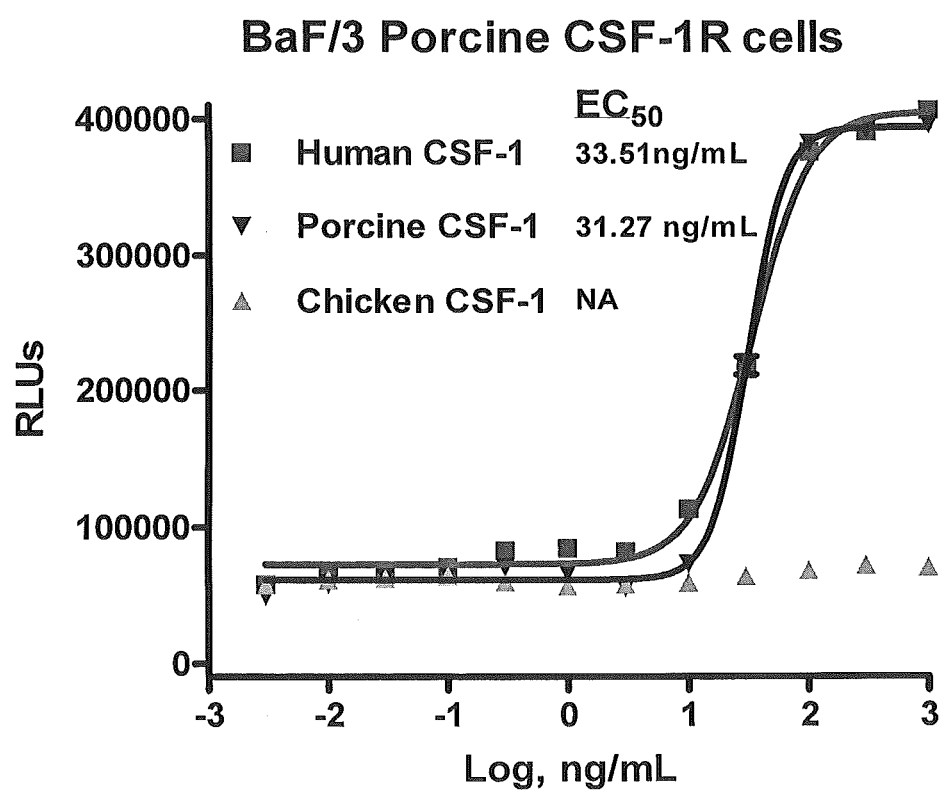

FIG. 10: Dose-Reponses data for all three CSF1 preparation on Porcine CSF1R-expressing BaF/3 cells.

METHODS

Bioinformatic Analysis
Sequences were identified using the databases at NCBI and the genome resources from the University of Santa Cruz and Ensemble. The translation of the zebra finch CSF1R gene was predicted using the GeneWise program and the chicken IL34 EST was analysed using ESTscan.

Cloning of Chicken and Zebra Finch cDNA Genes
RNA from chicken stage 20 embryo and zebra finch brain was extracted using TRIzol reagent, as described by the manufacturers (Invitrogen, Paisley, UK). cDNAs were cloned via RT-PCR using Superscript III reverse transcriptase and the TOPO TA cloning kit for sequencing (Invitrogen, Paisley, UK). 5' Rapid amplification of cDNA ends (5' RACE) of chicken and zebra finch CSF1, and zebra finch IL34, was carried out using the First Choice RLM-RACE Kit (Ambion, Warrington, UK). PCR products were cloned using the TOPO TA cloning kit for sequencing (Invitrogen, Paisley, UK). The 3' end of chicken CSF1 was cloned using a modified 3' Rapid amplification of cDNA ends (3' RACE) technique, 3' RACE LaNe (Park 2004).

Isolation of Chicken BACs Containing CSF1
A chicken probe for CSF1 was prepared using the Prime-a-gene kit (Promega, Southampton, UK) and hybridized to the chicken CHORI-261 BAC library overnight at 65° C. in 10% PEG8000; 7% SDS; 1.5×SSC. Filters were then washed twice in 2×SSC; 0.1% SDS and once in 0.5×SSC; 0.1% SDS at 65° C. and exposed to autoradiographic film for 1 week at room temperature. Six positive clones were identified: 44-I16, 68-D10, 22-M13, 171-K3, 171-N10 and 172-O23. 44-I16, 68-D10 and 171-N10 were confirmed by PCR. These clones were all end-sequenced and shown by Mat to map to Chr26.

Sequence Analysis
Clones were sequenced using BigDye Terminator v3.1 Cycle sequencing kit (Applied Biosystems, Foster City, Calif., USA) on an ABI 3730×1 sequencer.

Genetic Mapping of Chicken CSF1
A 437 bp genomic fragment of chicken CSF1 was amplified by the primers: ckcsfex4-for1: (SEQ ID NO: 8) GCGACTCT-GTCTGCTACGTG and ckcsfex5-rev1: (SEQ ID NO: 9) CGAAGGTCTCCTTGTTCTGC. Sequencing of the parental DNA from the East Lansing reference population (Crittenden et al. 1993) identified a SNP in exon4 (G/A in Red Jungle Fowl male; A/A in White Leghorn female) and sequencing of 52 backcross DNAs from confirmed CSF1 as mapping to Chr26. Linkage analysis was carried out using the Map Manager program (Manly and Olsen, 1999).

Phylogenetic Analyses
Amino acid sequences of annotated CSF1, IL34 and CSF1R genes from various taxa were aligned using the ClustalW software (Thompson et al. 1994) (Gonnet protein weight matrix, no ends gaps inactivated, default parameters). The secondary structures shown in the structure-based alignments were predicted using PSIPRED (Jones 1999), and the alignments performed by Domain Fishing (Contreras-Moreira and Bates 2002).

Whole Mount In Situ Hybridization
Fertilized White Leghorn eggs were collected weekly and incubated at 38° C. for between 3-6 days of development. Embryos were dissected into cold DEPC-PBS, staged as per (Hamburger and Hamilton 1992), and fixed immediately in 4% PFA/DEPC-PBS overnight, dehydrated into 100% methanol through graded methanol/PBS steps and stored at −20° C. Whole-mount ISH on embryos were carried out as per (Nieto et al. 1996). The CSF1R probe was made using the Ark-Genomics (Roslin, UK) clone 654 for template.

Chicken CSF1 and IL34 Expression

HEK293T cells (ATCC) and were cultured in DMEM (Sigma) supplemented with 10% heat inactivated (HI)-FCS, 2 mM L-glutamine, 0.1 mM non-essential amino acids and antibiotics (100 ug/ml penicillin, 100 ug/ml streptomycin). One day before transfection, $8\times10^5$ HEK293T cells were plated in 2 ml growth medium without antibiotics in a 6-well plate. The cells were transfected with Lipofectamoine 2000 as per product instructions. Cells were then incubated at 37° C. in a $CO_2$ incubator for 24 hr and transferred into 25 $cm^2$ dishes each containing 7 ml of growth medium (without antibiotics) for another 48 hr prior to harvesting the supernatant and lysing the cells in 2% SDS-10 mM Tris buffer. The cell extracts and supernatants were then mixed with Laemli buffer with or without DTT (5 mM final) or B-mercaptoethanol (5% final), run on a 4-12% gradient SDS-PAGE gel and transferred on PVDF membrane as per Bio-Rad apparatus instructions. The membrane was blotted using a mouse anti-v5 tag antibody (AbD Serotec) and an anti-mouse IgG HRP-conjugated (Cell Signaling Technology).

Bone Marrow Differentiation

Chicken bone marrow cells were obtained by flushing the marrow from 2 femurs and 2 tibias with PBS using a syringe and a blunt needle. For each condition, $\frac{1}{250}$ of total cells was pelleted and resuspended in 4 ml of complete RPMI (supplemented with 10% heat inactivated (HI)-FCS, 2 mM L-glutamine, 100 ug/ml penicillin, 100 ug/ml streptomycin) containing 20% supernatant from empty pEF6-, pEF6-cCSF1- or pEF6-cIL34-transfected HEK293T. Cells were plated in 60 mm Bacteriological plates and incubated at 37° C. in a $CO_2$ incubator for 12 days.

Intra- and Inter-Molecular Co-Evolution Analysis

To identify co-evolutionary patterns we used the parametric method based on correlated evolutionary patterns among amino acid sites previously published (Fares and Travers 2006b). To perform the analysis we used the software implementing this method CAPS version 1.0 (Fares and McNally 2006b). This method has proved to be successful in yielding meaningful results in several case studies, including those aimed at identifying co-evolution of membrane proteins (Fuchs et al. 2007), HIV gp120 and gp41 proteins (Travers et al. 2007) as well as Hsp70-Hop-Hsp90 system (Travers and Fares 2007). To estimate the probabilities and significance of the correlated evolutionary patterns among amino acid sites we used a large number of random samplings (1 million and 10 million random samples) and a small alpha value (0.001) to minimize false positive rate (type 1 error). CAPS also implements the step-down permutational procedure as described previously (Westfall and Young 1993; Travers and Fares 2007) to correct for multiple testing. The scores for the amino acid substitutions were obtained using the appropriate blocks substitution matrix (BLOSUM80) (Henikoff and Henikoff 1992) depending on the similarity of our protein sequences. All amino acid sites reported in the co-evolutionary analyses present the positions in the protein from the reference sequence (human).

Visualization of Co-Evolutionary Networks

We used the software Cytoscape (version 2.6.1) (Shannon et al. 2003) to visualize the co-evolutionary networks identified by CAPS. Cytoscape was originally designed to visualize bimolecular interaction networks. This tool however can be used to visualize any data that describes interactions between objects. CAPS can produce four files containing information of co-evolutionary networks and compensatory mutations. We used this program to generate the networks of correlation between co-evolving amino acids and used the correlation coefficients generated in CAPS to determine the coloring patterns of the linking lines between nodes (amino acid residues).

Cloning of Chicken CSF-1 Gene

The sequence corresponding to the active fragment of chicken CSF-1 (SEQ ID NO: 10) (NSYCQQI-ITERHLDHLQELADTQMQQPGTVSFRFISKMRL-SDSVCYVKAAFPLLGTILN RTTFKENSTNANKMK-TVRKMYENIDENVDPCIRDEDDKEHALSEMCFE-EFTTSPYEML VLVRQFFQDIKQLLQNKETFEKDC-SQVYRSACAGPRQHSSSP) was codon optimized for expression in E. coli and synthesized by Blue Heron Biotechnologies (WA, USA). The sequence was engineered with a BspHI restriction site at the 5' end and an EcoRI restriction site at the 3' end and cloned into the expression plasmid pET-28(b) using the complimentary restriction sites NcoI and EcoRI. The resulting plasmid, pTLW54, was transformed into MAX Efficiency® DH5α™ Chemically Competent E. coli according to the manufacturer's protocol (Invitrogen, CA, USA). A kanamycin resistant transformant was selected and the plasmid sequenced to verify the error-free ORF. The pTLW54 plasmid was isolated via QIAprep® spin miniprep kit (Qiagen, CA, USA) according to the manufacturer's recommendations and transformed into One Shot® BL21 Star™ Chemically Competent E. coli (Invitrogen, CA, USA). The chicken CSF-1 gene within pTLW54 was again sequenced to verify error-free ORF.

Expression of Chicken CSF-1 Protein

An overnight LB/$Kan^{50}$ broth of pTLW54/One Shot® BL21 Star™ E. coli incubating at 37° C. with 225 rpm shaking was refreshed 1:10 into 1 L of LB/$Kan^{50}$ broth. The refreshed culture was incubated with 225 rpm shaking at 37° C. for two hours to ensure mid-log phase growth. Protein expression was induced with 1 mM IPTG, final concentration, with incubation conditions continued at 37° C. and 225 rpm shaking. After 2 hours induction, the culture was centrifuged and the E. coli pellet was stored at −80° C. Prior to centrifugation, aliquots were analyzed for expression of protein compared to a non-induced control. Soluble and non-soluble protein fractions were analyzed on a 4-12% Bis-Tris NuPAGE gel run in MES buffer. As shown in the FIG. 6, the induced culture produced a band of approximately 18.7 kDa in the non-soluble protein as expected.

Purification and Processing of Chicken CSF-1 Protein

Frozen cell pellets were broken and inclusion bodies were washed to near homogeneity. Monomeric chicken CSF-1 protein was purified using a 2.6×60 cm Superose 12 size exclusion chromatography column (SEC) in a 50 mM Tris, pH 8.5, 5 mm EDTA, 7M guanidine. The eluted chicken CSF-1 was diluted 10-fold in the 7M guanidine buffer and allowed to refold via sequential dialysis by addition of 50 mM Tris, pH 8.5, 100 mM NaCl, 5 mM EDTA, 1 mM oxidized glutathione, 2 mM reduced glutathione buffer through 8 steps resulting in a final guanidine concentration of 0.15 M. The refolded chicken CSF-1 was concentrated and the monomeric species was purified using a 1×30 cm Superose SEC column run in PBS. The monomeric protein was concentrated to 0.58 mg/ml and analyzed by 16% SDS-PAGE with and without BME as shown in the FIG. 7. Aliquots of purified chicken CSF-1 were stored at −80° C.

Results

Identification of Avian CSF1 Genes

There is currently no annotated CSF1 gene in the chicken genome, but the region containing the mouse CSF1 gene displayed synteny with the chicken suggesting there was a gap in the chicken genome assembly. Based upon privileged access to the zebra finch genomic sequence, it was possible to identify a clear CSF1 ortholog (starts in exon3) [Chr26: 24187-27419, July 2008 assembly] (GQ249405). This, in turn, led to the identification of a partial CSF1 sequence in the chicken EST collection at the Roslin Institute. A complete ORF was obtained by 5' and 3' RACE to determine the full CDS. CSF1-containing BACs were also identified and end-sequenced to confirm mapping to Chr.26. The CSF1 locus is indeed predicted to be in a gap in the chicken genome assembly, since in the zebra finch the flanking gene order is the same as in mammals. The newly-identified avian CSF1 genes each contain 8 exons. The zebra finch gene encodes a protein of 489 amino acids. Two transcripts have been identified in the chicken—one encoding a protein of 490 amino acids, and the other comprising 270 amino acids (GQ249403 and GQ249404). The shorter transcript is missing a substantial part of Exon 6. In mammals, this exon encodes a large domain that contains a proteolytic cleavage site which permits the release of CSF1 from a membrane-anchored precursor. The shorter transcript would encode the membrane-anchored cell surface form of CSF1, which cannot be cleaved. The exon 6 of chicken CSF1 also contains the unique glycosaminoglycan (chondroitin sulfate) addition site (SGXG/A) found in the mammalian genes. Hence, the basic biology of CSF1, involving secreted and membrane-anchored forms with variable post-translational modification and distinct functions (Dai et al. 2004; Jang et al. 2006; Nandi et al. 2006) appears to be conserved in the chicken.

Conserved Structure of Avian CSF1

In order to assess whether the avian CSF1 sequences identified are functional orthologs of mammalian CSF1, a multiple alignment of deduced amino acid sequences across species was performed using the ClustalW software (Thompson et al. 1994) (Table 1). The six cysteine residues responsible for the three intramolecular disulfide bonds (Pandit et al. 1992) are conserved in birds, but the cysteine forming the inter-chain disulfide bond that is located at the dimer interface and conserved through all species including zebrafish and gold fish (Hanington et al. 2007) is not conserved in birds. The alignment of the cysteines and predicted helices highlight the contact residues for CSF1 bound to CSF1R deduced from the co-crystal in mouse (Chen et al. 2008), some of which are clearly divergent in birds. In particular, the Asp91 and 94, Gln113, Glu114, and Asn117 (position numbers referring to the mouse sequence in Table 1) are not conserved or have semi-conservative substitutions. Immediately downstream of these binding sites, the bird sequences have additional amino acids that are not present in the mammalian sequences. This alignment also highlights the substitution of R111 in mouse, with Q in human, which could explain why the human ligand works on mouse cells, but not vice versa (Bonifer and Hume 2008).

Figure 1B:
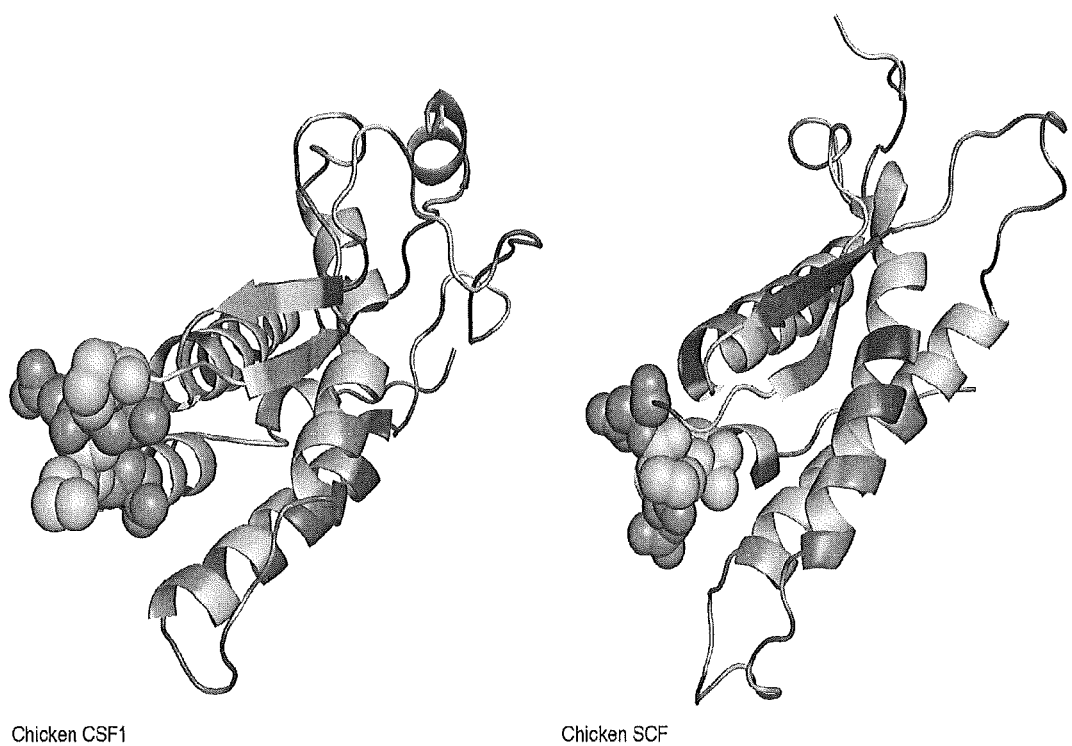

To verify avian CSF1 structure predictions, 3D-models in PDB format were generated with 3D-Jigsaw using structure-based alignments (performed by Domain Fishing) (Bates et al. 2001). The PDB files obtained were viewed in FirstGlance in Jmol and the models rendered by PyMol using Polyview-3D (Porollo and Meller 2007). The avian CSF1 are predicted to have the same four-helix bundle structure as the well described mammalian CSF1 (Pandit et al. 1992). In FIG. 1A, the chicken CSF1 model is compared with the published mouse structure (Chen et al. 2008). Although the overall topology is conserved from mammals through birds, all the differences found in the sequence alignment translate into structural changes. Hence, the CSF1R-binding site 1 of chicken CSF1 comprises different charges from the mouse binding site 1 as the non-conserved amino acid substitutions are precisely positioned to contact with the receptor (red arrows). Moreover, the extra residues found in the chicken sequence are predicted to create a protuberance making the positively charged Arg122 stick out between the binding sites 1 and 2 (black arrow). As previously mentioned, the cysteine forming the inter-chain disulfide bond in mammals (labelled Cys on the mouse structure) is absent from the chicken CSF1, resulting in non-covalently associated homodimers. This is also the case for the closely related Stem cell factor (SCF) in mammals as well as in birds (Arakawa et al, 1991). These proteins can form stable dimers and induce receptor dimerization because of the large contact surface area between the monomers (Jiang et al. 2000). Interestingly, the contact surface between the chicken CSF1 dimers is very similar to that of chicken SCF. They both contain exposed hydrophobic residues, as shown in FIG. 1B where the amino acids present on the dimer interface were rendered as spacefill.

Identification of Avian IL34 Genes

There is an obvious chicken ortholog of human IL34 in the chicken genome, and we have identified a chicken cDNA within the Ark-Genomics (Roslin, UK) collection which maps to chromosome 11 and contains the full-length IL34 CDS (Genbank accession no. BX931154). This chicken sequence allowed for the identification of the orthologous zebra finch gene within the genome sequence [Ch11: 5,575, 502-5,577,560; July 2008 assembly] (GQ249406). The avian genes each contain 6 exons, the chicken gene encoding a protein of 178 amino acids, and the zebra finch gene encoding 180 amino acids.

Conserved Structure of IL34

Figure 2A:
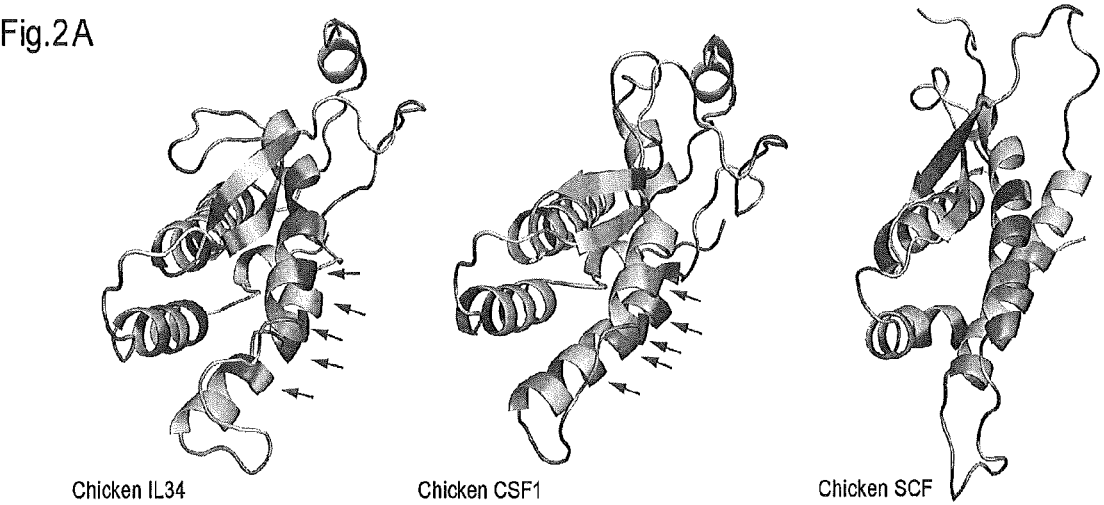
Figure 2B:
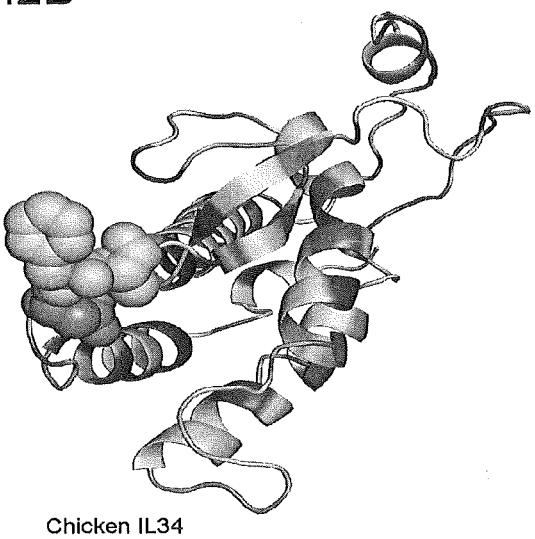

At the amino acid sequence level, IL34 is considerably better conserved across species than CSF1 (Table 2). Although the paper describing human IL34 claimed that it was structurally novel (Lin et al. 2008), our own analysis suggests that IL34 is a four-helix bundle protein just like the well-described CSF1 (Pandit et al. 1992; Taylor et al. 1994; Chen et al. 2008). It is true that IL34 and CSF1 can be aligned with each other with only weak primary homology but they have a very similar predicted topology. A 3D-model of the chicken IL34 was generated with 3D-Jigsaw using structure-based alignments (performed by Domain Fishing) (Bates et al. 2001). The resulting PDB file was viewed in FirstGlance in Jmol and the model rendered by PyMol using Polyview-3D (Porollo and Meller 2007) (FIG. 2A). For structural comparison, a model for the chicken SCF was created following the same procedure, and the chicken CSF1 model shown in FIG. 1 was also included in the figure. This structural analysis of the derived protein sequence predicts a molecule that lacks all the seven strategically positioned cysteines. IL34 contains some generally conserved cysteine residues, but these are not positioned and matched together in order to form intra-chain disulfide bonds. The cysteine required for the formation of an inter-chain disulphide bridge is not found on the dimer interface as in mammalian CSF1, but that region contains exposed hydrophobic residues (FIG. 2B). The corresponding amino acids that constitute the receptor-binding site 1 on CSF1 are pointed out by red arrows. These residues are totally different from those in IL34, immediately suggesting an alternate binding mechanism from that of CSF1 protein.

Identification of the Zebra Finch CSF1R Gene

In the chicken genome on chromosome 13, there is an annotated CSF1R gene (Ensembl ID: ENSGALG00000005725), occupying the same position as in mammals, immediately 3' of the closely-related PDGFRB gene (Ensembl ID: ENSGALG00000021313). The availability of the chicken sequence allowed us to identify the orthologous sequence in the zebra finch genome [Chr13: 6,954,381-6,972,446; July 2008 assembly] (GQ249407). This gene contains 21 exons like the chicken CSF1R, and codes for a protein of 967 amino acids, which again is the same length as the chicken CSF1R.

Evolutionary Conservation of CSF1R

Figure 3A:
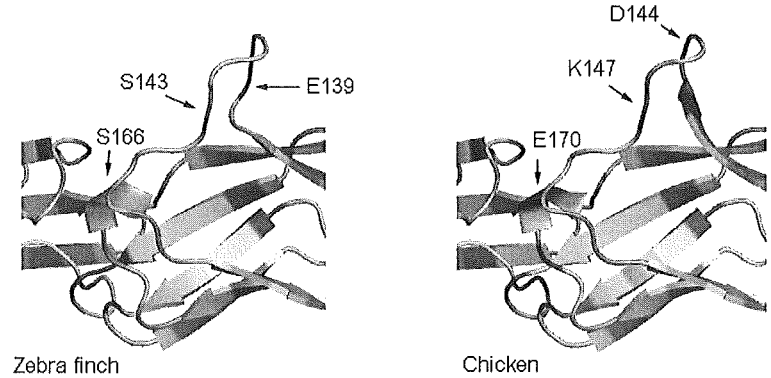
Figure 3B:
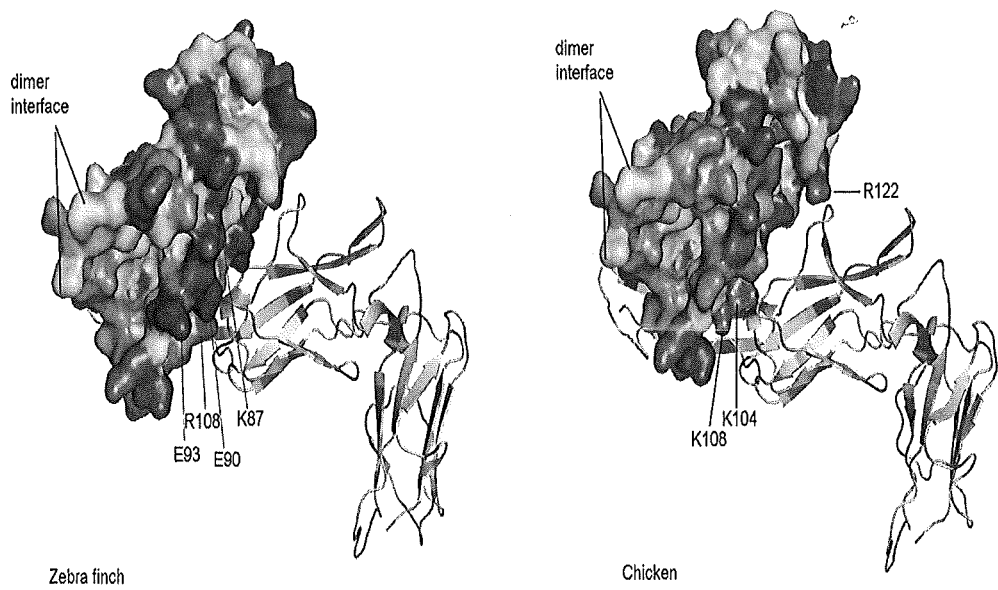
Figure 3C:
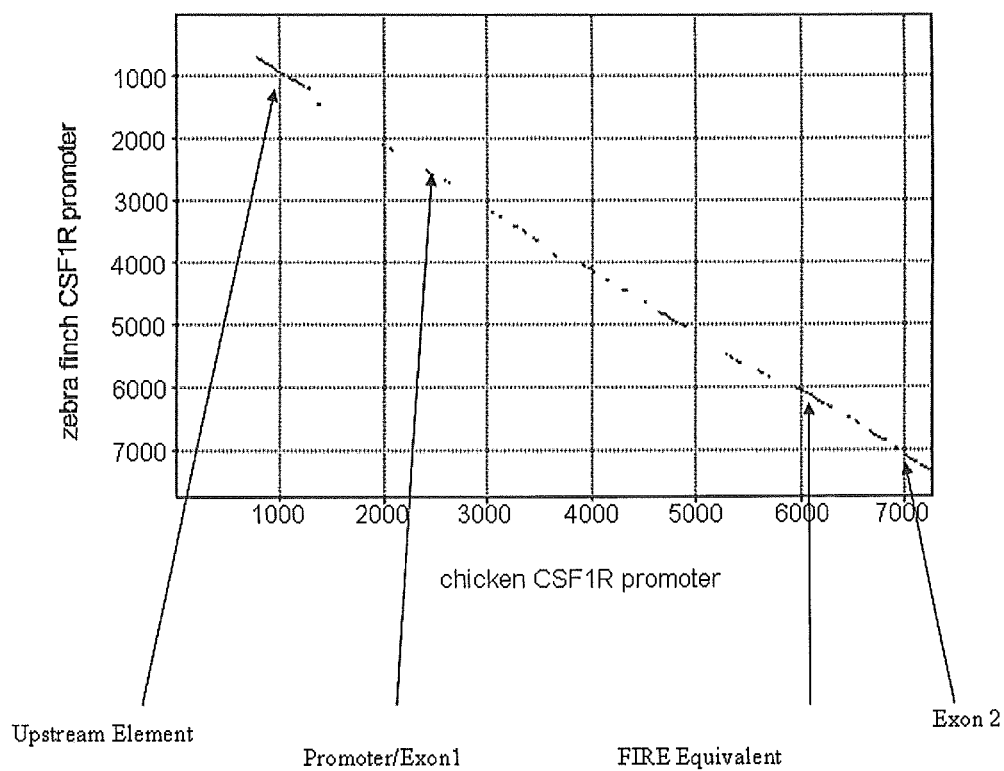

A new multiple alignment of amino acid sequences across species was performed using the ClustalW software to examine the homology between the bird CSF1R and the mammalian orthologs (Table 3). As expected, the intracellular tyrosine kinase domain (aa 540 to 977) of the receptor is extremely conserved through all species, including birds. Amongst the residues that are not conserved however, is the cysteine 665 (indicated by an arrow in table 3) which is substituted for an arginine only in birds. This substitution may underlie our finding that chicken CSF1-induced macrophage growth is not blocked by a kinase inhibitor, GW580 (V Garceau, unpublished) that inhibits mammalian CSF1R activity (Irvine et al. 2006). Most of the residues composing the CSF1-binding sites 1 and 2 (labeled respectively with "+" and "o" symbols in table 3) deduced from the mouse CSF1R/CSF1 co-crystal are not conserved between the two birds. Some of the amino acid substitutions observed between the two birds are illustrated in FIG. 3A, where 3D-models of the CSF1-binding site 1 on the D2 domain of the zebra finch (left) and the chicken (right) CSF1R are presented. As with the ligands, the models were created using 3D-Jigsaw and Polyview-3D. A more general view of the D1-D3 domains of these same receptors with a superimposed structure of their respective CSF1 molecule is presented in FIG. 3B. The receptors are shown from the same angle as in FIG. 3A, and the chicken CSF1 structure is the same model as in FIG. 1A rendered as surface instead of cartoon, with the dimer interface labeled for orientation. The zebra finch CSF1 structure was produced using the same settings, and the superimposition angle is based on the co-structure of the mouse CSF1:CSF1R complex (Chen et al. 2008). In this figure, the amino acid substitutions in the zebra finch (left) and chicken (right) receptors are put in context with those present in their respective CSF1 ligand. This high level of divergence is not surprising since zebra finches and chickens are not part of the same taxonomic order. As with primate and rodent CSF1, we predict that the zebra finch CSF1 will not activate the chicken receptor, or vice versa, due to the substantial changes in charge density in the binding sites.

Transcriptional Regulation of Avian CSF1R

Figure 3D:
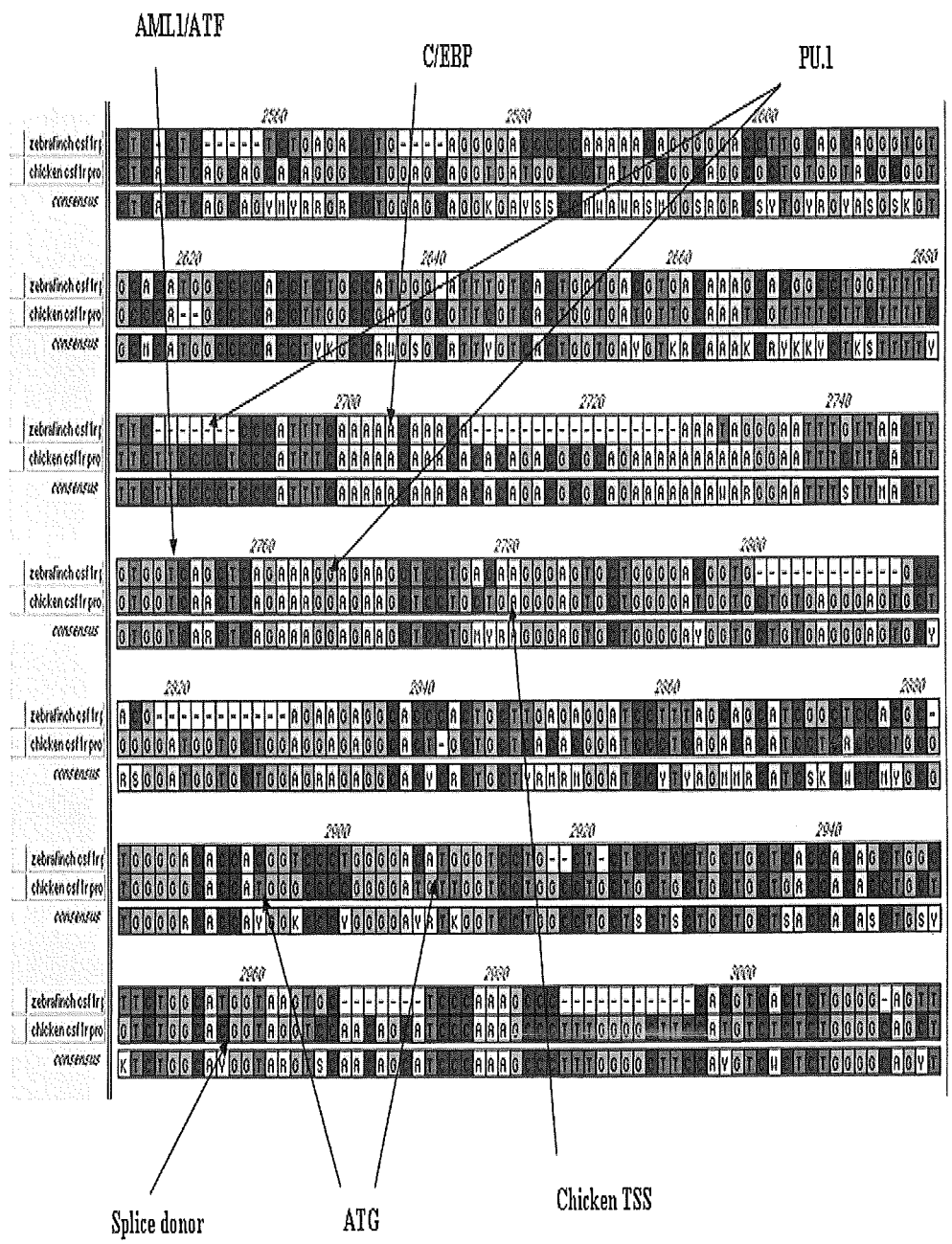
Figure 3E:
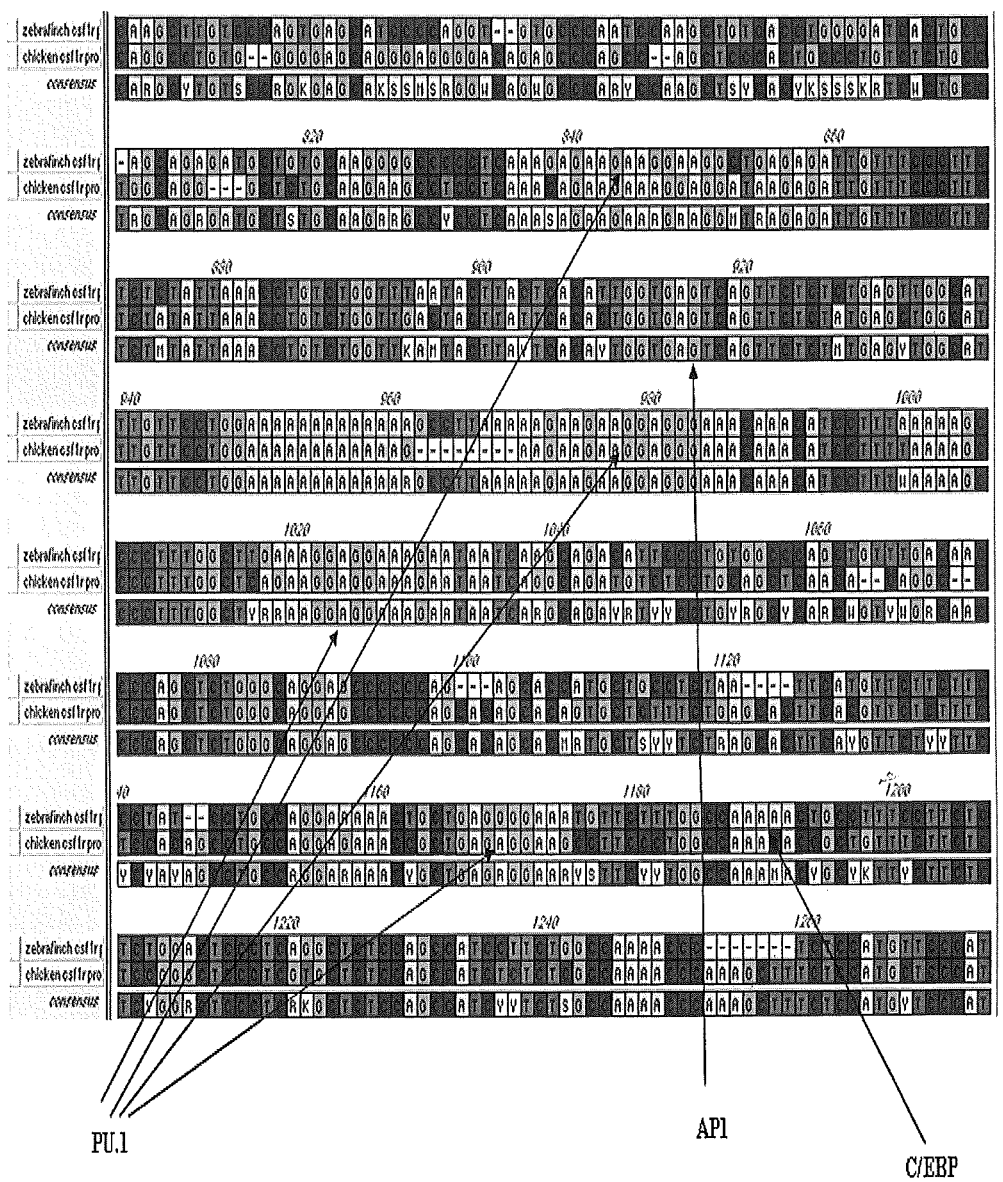

The mammalian CSF1R loci contain a conserved macrophage-specific promoter region, and a remarkably conserved enhancer (FIRE) in the first intron that is required for macrophage-specific expression of a transgene (Sasmono et al. 2003). These elements are not evidently conserved in birds. However, the transcription factors required for macrophage gene expression, such as PU.1, have clear chicken orthologs. To assess the likelihood of CSF-1R being a macrophage regulator in birds, we first assessed the transcriptional regulation of the chicken and zebrafinch genes. Passeriformes and galliformes are separated by around 100M years of evolution, about the same as rodents and humans (www.timetree.org). Because of this distance, evolutionary conserved, non-coding regions provide strong indications of the location of functional promoters and enhancers; in mammals the FIRE (fms intronic regulatory element) is more conserved than any of the exons (Himes et al. 2001). The intron-exon structure of avian CSF1R is the same as in mammals (www.ensembl.org), with the ATG start codon located in the first exon. Like the mammalian CSF1R promoters, the two avian CSF1R proximal promoters are not highly conserved, but both are purine-rich and TATA-less. In both bird species, there are two very highly conserved regions, upstream and downstream of the promoter. This is shown in the Pustell DNA matrix alignment of FIG. 3C. The downstream element is in the same relative location within the first intron as the mammalian FIRE (Himes et al. 2001). The candidate avian FIRE sequence cannot be aligned with the mammalian FIRE, but contains the same basic elements. These regions contain multiple repeats of consensus sequences in common with mammalian CSF1R and FIRE, including candidate binding sites for PU.1 and other Ets factors, API, C/EBP, Sp1 and AML1 (FIGS. 3D and 3E). Each of these transcription factors is expressed in haematopoietic cells in chickens (Faust et al., 1999; Bakri et al. 2005). These findings suggest that avian CSF1R is controlled in basically the same manner as in mammals, despite the reassortment of the cis-acting individual elements.

Expression Pattern of CSF1R in Chick Embryo

Figure 3F:
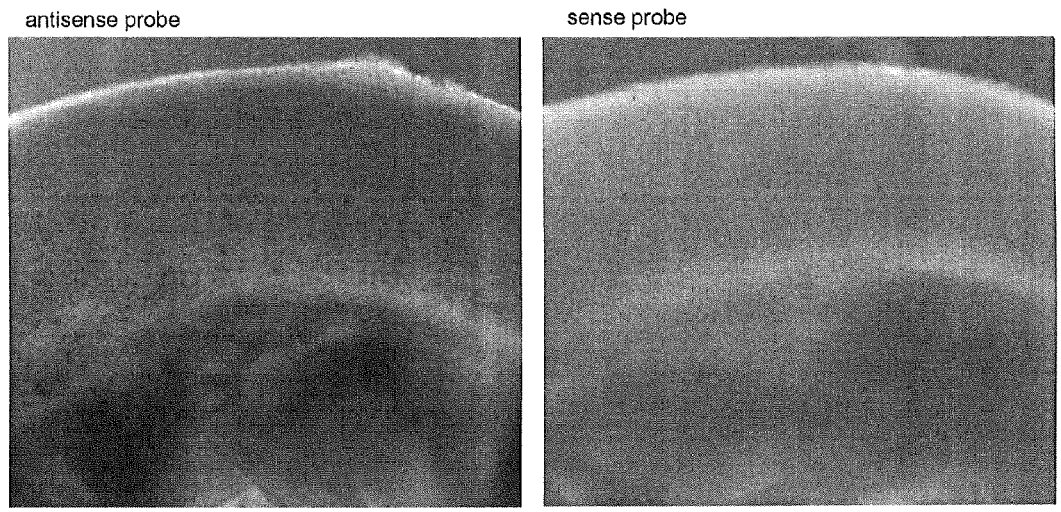

The analysis of conserved regions identifies candidate enhancers of the chicken CSF1R locus, and suggests that the gene is likely to be expressed specifically in macrophages. To confirm that prediction, we carried out whole mount in situ hybridization of chicken embryos at 20 HH or 3.5 days of development, the wing bud stage (FIG. 3F). This stage corresponds to 11.5 dpc in the mouse embryo. As in the mouse (Lichanska et al. 1999), and consistent with macrophage distributions in *Xenopus* (Tomlinson et al. 2008), the chicken csflr mRNA is expressed in a speckled pattern all over the embryo, consistent with restriction to the numerous macrophages in every organ of the body (left panel).

Activation of the Chicken CSF1R by CSF1 and IL34

The expression of CSF1R on the cell surface is amongst the earliest events in macrophage lineage commitment (Tagoh et al. 2002), and CSF1 is commonly used to grow pure populations of macrophages from mouse bone marrow (Bonifer and Hume 2008). Both ligands were therefore tested for differentiation of chicken bone marrow cells. The chicken CSF1 (first six exons) and IL34 genes were cloned in the pEF6 vector, providing them with a C-terminal tag for detection, and transfected into HEK293T cells. The expressed proteins within the cell and supernatant were detected by Western blotting (FIG. 4). In the case of CSF1, three apparent molecular entities are seen in the non-reduced supernatant, and the lowest apparent MR (ca. 60 kD) is mostly present in the cells; suggestive that the secreted protein is processed in the ER and glycosylated, maybe even as a proteoglycan. In the case of IL34, the protein was detected in the cells and supernatant as a doublet, with the higher apparent MR being more abundant than the lower MR, suggesting that IL34 is glycosylated in this system. The amount of epitope-tagged cIL34 detected in the supernatant was considerably less than in the cell lysates. This might be due to some proteolytic cleavage of the C-terminus by trypsin-like proteases in the secretory pathway or medium as a string of basic amino acids are found at the C-terminal of IL34, just upstream of the v5 tag. The supernatant from the transfected HEK293T cells, or cells transfected with the vector only, was added to bone marrow cells obtained by flushing the marrow from a chicken femur, and the cells were incubated for ten days. Around Day 3, cells growing in the presence of chicken CSF1 or IL34 became adherent, and by Day 12, the dishes were confluent. No bone marrow cells survived in the control dish containing supernatant from empty pEF6-transfected HEK. Hence, both CSF1 and IL34 offer the possibility of growing macrophages from chicken marrow for functional studies; bone marrow-derived macrophages have been a mainstay of macrophage functional studies in the mouse (Bonifer and Hume 2008). Together, the data indicate that the function of CSF1R and its two ligands is conserved in birds.

Co-Evolution of CSF1R, CSF1 and IL34

The extracellular domain of CSF1R is quite divergent among species, as is CSF1. Even between mice and rats, IL34 is considerably better conserved, and yet activates the same receptor as CSF1. The divergence of CSF1/CSF1R could be related to the fact that (a) CSF1 is massively inducible in the circulation in response to innate immune stimuli such as LPS, and (b) the CSF1R extracellular domain is cleaved from the cell surface in cells responding to a range of TLR agonist, through the actions of ADAM14/TACE (Sester et al. 1999; Rovida et al. 2001). So, one might argue that CSF1 is required for effective innate immune responses and is therefore under immune selection. Indeed, Epstein-Barr virus encodes a soluble CSF1R antagonist, BARF1 (Strockbine et al. 1998). This raises the interesting evolutionary question of exactly how two ligands could evolve with a single receptor. In theory, and provided the overall structure is conserved, alterations in contact residues in the ligand should be compensated by alterations in the receptor to preserve binding affinity, and within a sufficiently large sample, there should be a correlation matrix between amino acids on the partners. Incorporating the alignments presented in Tables 1, 2 and 3, and published PDB structures for CSF1/CSF1R it was possible to distinguish functional co-evolution from phylogenetic or random co-variation in order to calculate a correlation coefficient (Fares and Travers 2006a). The CAPS software was used to identify amino acid sites having a strong correlation coefficient (Fares and McNally 2006a), and the networks of these co-evolving residues are shown in FIG. 5A. The strength of the correlation coefficient for specific site pairs is indicated by the color of the line connecting them, and the amino acid positions numbering follows the human sequences as reference. Unexpectedly, the only significant correlations were found between CSF1R and the more conserved of the two ligands, IL34. Moreover, no sign of intra-protein co-evolution was found in any of the three proteins.

IL34 Binding Mode of CSF1R

Figure 5B:
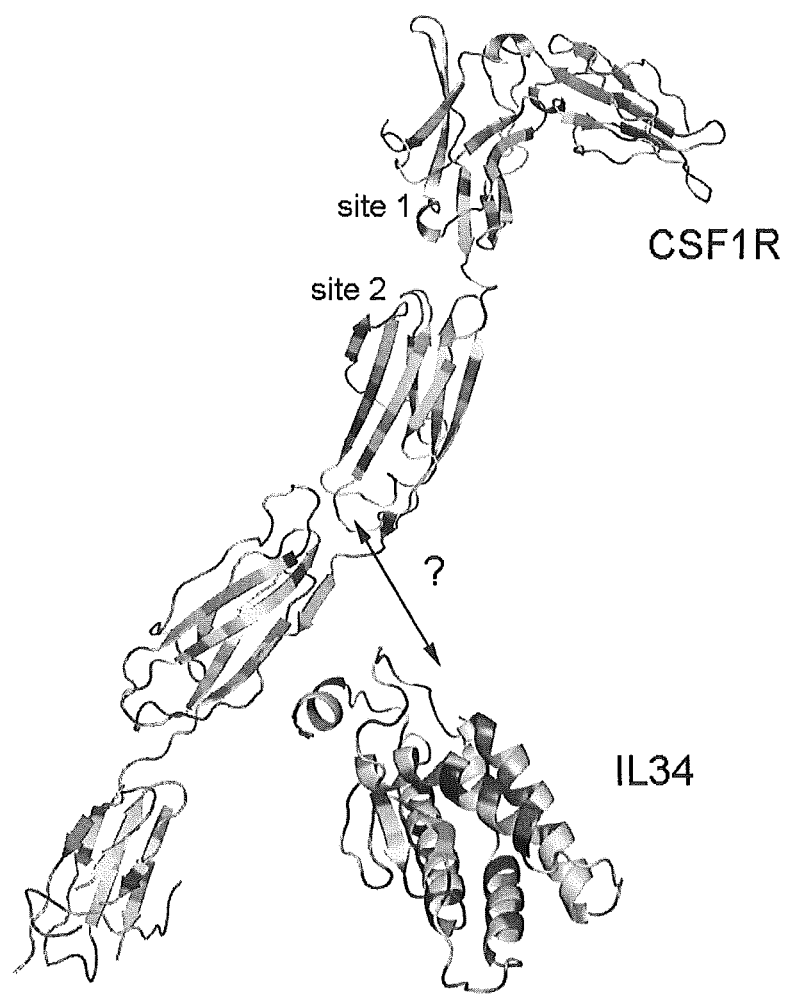

None of the co-evolving amino acid positions identified by CAPS in CSF1R are located within the CSF1-binding sites which are in D2 and D3 domains (Chen et al. 2008). Instead, they are concentrated at the junction between D3 and D4. In a similar manner, the co-evolving residue positions in IL34 are located outside the corresponding CSF1R-binding site of CSF1. All the co-evolving residues appearing in the networks of FIG. 5A were mapped on the chicken CSF1R and IL34 structures (FIG. 5B). The chicken CSF1R D1-D5 structure was generated as a chimera of two PDB files generated by 3D-Jigsaw for the chicken receptor: D1-D3 using the mouse CSF1R structure as template (3ejj), and D1-D5 using the human KIT structure as template (2e9w). The two models were then superimposed to create the chicken CSF1R D1-D5 structure. The chicken IL34 model is the same one as in FIG. 2, viewed in a slightly different angle. The corresponding co-evolving residue positions in chicken were deduced from the alignment in Table 2, then highlighted in blue using Polyview-3D. The co-evolution of specific sites on CSF1R and IL34 can be interpreted as a possible binding mode between this uncharacterized new ligand and the receptor. Hence, we can speculate that IL34:CSF1R binding site interface consists of the CD loop of IL34 and the region around the D3-D4 junction of CSF1R.

Assessment of Bioactivity Via BaF/3 Cell Based Assay

Recombinant chicken CSF1 has demonstrable specific bioactivity as demonstrated when titrated on to factor-dependent parental BaF/3 cells and BaF/3 cells expressing chicken CSF1R or porcine CSF1R. Parental BaF/3 cells, chicken CSF1R expressing BaF/3 cells or porcine CSF1R expressing BaF/3 cells that had been cultured in RPMI 1640 media+10% HI FBS+GlutaMax+pen/strep (20 U/mL and 20 micrograms/mL) and 10 ng/mL recombinant murine IL-3 were collected, washed and plated in 96-well microtitre plates at 20K cells per well and cultured overnight. The following day, recombinant chicken CSF1 was titrated against all three cell lines. As controls, recombinant porcine CSF1 and recombinant human CSF1 (Sigma 6518) were also titrated against all three cell lines. Cell assays were then incubated for a further 48 hrs afterwhich cell survival/proliferation was assessed using the TireGlo assay system (Cell TiterGlo; Promega G7571). None of the CSF1 preparations promoted survival or proliferation in the BaF/3 parental line (FIG. 8). Whilst porcine and human CSF1 preparations did not promote survival/proliferation of BaF/3 cells expressing the chicken CSF1R, the chicken CSF1 preparation did show bioactivity (EC50=ca. 20 ng/mL) through the chicken CSF1R as demonstrated by robust survival and proliferation when titrated onto the chicken CSF1R expressing BaF/3 line (FIG. 9). Both Porcine and human CSF1 preparation were bioactive as they had equimolar bioactivity (EC50=30 ng/mL) on the porcine CSF1R-expressing BaF/3 cell line as demonstrated in FIG. 10.

Discussion

The structural basis of the interaction between CSF-1, IL34 and CSF-1R presents a scientifically interesting phenomenon from an evolutionary point of view. Current genomics efforts now provide sequences from more than fifteen species for both ligands and the receptor. From these sequences, it is apparent that the interaction is conserved evolutionarily back as far as fish. By aligning the sequences, and examining the tolerance of different residues at significant positions, it is possible to identify particular amino acids in the receptor that vary in conjunction with a given residue of CSF-1 or IL34. The ability of CSF-1 from one species to induce growth and survival of macrophages (or cells transfected with the receptor) from another species adds weight to predictions based on evolutionary conservation. For instance, mouse CSF-1 cannot bind human CSF-1R, yet human CSF-1 can bind and activate mouse CSF-1R (Koths 1997). In fact, human CSF-1 can activate CSF-1R from all species for which it has been tested (human, mouse, feline, sheep and dog), whereas mouse CSF-1 can activate all non-primate CSF-1R tested (mouse, feline, sheep and pig), but not human CSF-1R (Stanley and Guilbert 1981; Woolford et al. 1988; Tamura et al. 1990; Francey et al. 1992; Ramsoondar et al. 1993; Yoshihara et al. 1998; Abrams et al. 2003). The only contact amino acid that is not conserved in mammals is mouse R111, which is Q in humans, and varies in other species. Bovine CSF-1 causes growth of murine bone marrow macrophages, presumably through activation of murine CSF-1R (Yoshihara et al. 1998). Chicken (or at last M-CSF bioactivity in chicken cell conditioned medium) and feline CSF-1, conversely, are unable to activate the human and mouse CSF-1R, and are restricted to activating the receptor of their own species (Tamura et al. 1990; Tamura et al. 1991).

Recent studies identified the CSF1 genes of several fish species, and provided evidence of primitive duplications of the gene in these species (Wang et al. 2008). All of the piscine CSF1 genes had almost complete divergence of the mammalian contact residues implied from the mouse CSF1/CSF1R co-crystal structure. In the current study, we have identified and expressed the chicken CSF1 and IL34 genes, provided evidence that CSF1R is expressed in chicken macrophages as it is in mammals (and most likely controlled in a similar manner (FIGS. 3C-3F), and that recombinant factors can produce pure macrophage cultures from bone marrow precursors. Hence, the biology of the CSF1/IL34/CSF1R triad is also conserved in another class of vertebrates, the birds. Molecular modeling suggests that CSF1 has a conserved structure in birds and mammals, and in contrast the published study (Lin et al. 2008) suggests that IL34 also shares that topology characterized by a four-helix bundle (Pandit et al. 1992). Although the fact that IL34 lacks all the cysteines forming the distinctive intra-chain disulfide bonds in CSF1, other growth factors such as SCF, GM-CSF and GH all have only one or two intra-chain bonds, and yet have that same four-helix topology (Pandit et al. 1992).

It was already known that IL34 binds CSF1R (Lin et al. 2008), and the finding of a structure similar to that of CSF1 could have lead to the conclusion that they were both sharing the same binding sites on CSF1R. This is not compatible with the sequence of IL34, wherein the contact points identified from the CSF1/CSF1R co-crystal structure are completely variant. The co-evolution study performed here revealed a new perspective. When identified on the 3D structure of the proteins, the co-evolving residue positions uncovered by CAPS are grouped together in distinctive regions. On IL34, most of them are located at the end distal to the dimer interface, in particular on a flexible loop between helix C and helix D. None of the co-evolving residues are situated in the corresponding binding site on CSF1. On CSF1R, the majority of them are positioned at the junction of D3 and D4. If brought together, these two binding sites would naturally fit with each other. Moreover, it is known that the CSF1R D4 lacks the characteristic disulfide bond of Ig-like domains that connects the beta-sheets, and is likely to have greater flexibility (Blechman et al. 1995). Even the recently published model for CSF1R dimerization and activation could accommodate such an alternative binding mode for IL34 (Chen et al. 2008). Interestingly, this binding mode is reminiscent of the binding of other 4-helix bundle factors (GH, GM-CSF, EPO) to their receptors, involving sites between helices, and binding within an intra-domain cleft that is rather closer to the plasma membrane than the domain D2/3 cleft of CSF1R. Activation models of CSF1/CSF1R suggest that dimerization permits interactions between the two domain D4s, leading to a conformational change that generates signaling (Chen et al. 2008). Could IL34 thereby generate a distinct signal? In the case of the GHR, distinct mutations in the extracellular domain that alter conformation can lead to selective loss of particular signaling pathways in transfected FDCP1 cells (Rowlinson et al. 2008). The extracellular domain of CSF1R linked to the intracellular domain of GHR can provide a CSF1-dependent growth-promoting signal to the same factor-dependent cells (M J Waters, D A Hume, unpublished). So, it is conceivable that the two ligands could signal through the same receptor to generate signals that only partly overlap.

The different binding mode of CSF1 and IL34 is implied by the fact that, even though changes of charge in CSF1 binding sites are matched by changes of opposite charges in the receptor binding sites, there is no significant correlation coefficient between them. The weak binding of CSF1 to CSF1R is based on salt bridges, and simply requires the presence of opposite charges at the site to occur. This does not have to involve a strict co-evolution of matching amino acids. The binding of IL34 to CSF1R, however, could be based on hydrogen bonds necessitating perfectly complementary, thus co-evolving, residues.

In addition to suggesting alternative binding sites for IL34 and CSF1R, the co-evolution study gives us a hint about a functional difference between CSF1 and IL34. Indeed, the fact that a correlated evolutionary co-variation with CSF1R can only be detected for IL34 means that the latter is subjected to stronger selective constraints than CSF1. In other words, a change in the genetic composition of IL34 would necessarily involve a reciprocal evolutionary change in the receptor as the consequences of any loss of activity would be more dramatic than a similar loss for CSF1. Furthermore, it also suggests that CSF1 is free to evolve more quickly than IL34, and without the receptor coevolving with it. These interpretations, taken together with the better conservation of IL34 and the rather different expression pattern of IL34 compared to CSF1 suggest that IL34 might perform a more trophic role.

Macrophages have many apparent roles in embryonic development (Lichanska and Hume 2000; Rae et al. 2007) but studies of their function in mammals have been constrained by the inaccessibility of the embryo, and the fact that CSF1 is produced by the mother and transmitted across the placenta. We have now identified the key regulators that are likely to control avian myelopoiesis and will be able to take advantage of the accessibility of chicken development in ovo to manipulate expression and function of these genes.

REFERENCES

Abrams K, Yunusov M Y, Slichter S, Moore P, Nelp W B, Burstein S A, McDonough S, Durack L, Storer B, Storb R et al. 2003. Recombinant human macrophage colony-stimulating factor-induced thrombocytopenia in dogs. *Br J Haematol* 121(4): 614-622.

Arakawa T, Yphantis D A, Lary J W, Narhi L O, Lu H S, Prestrelski S J, Clogston C L, Zsebo K M, Mendiaz E A, Wypych J et al. 1991. Glycosylated and unglycosylated recombinant-derived human stem cell factors are dimeric and have extensive regular secondary structure. *J Biol Chem* 266(28): 18942-18948.

Avery S, Rothwell L, Degen W D, Schijns V E, Young J, Kaufman J, Kaiser P. 2004. Characterization of the first nonmammalian T2 cytokine gene cluster: the cluster contains functional single-copy genes for IL-3, IL-4, IL-13, and GM-CSF, a gene for IL-5 that appears to be a pseudogene, and a gene encoding another cytokinelike transcript, KK34. *J Interferon Cytokine Res* 24(10): 600-610.

Bakri Y, Sarrazin S, Mayer U P, Tillmanns S, Nerlov C, Boned A, Sieweke M H. 2005. Balance of MafB and PU.1 specifies alternative macrophage or dendritic cell fate. *Blood* 105(7): 2707-2716.

Bates P A, Kelley L A, MacCallum R M, Sternberg M J. 2001. Enhancement of protein modeling by human intervention in applying the automatic programs 3D-JIGSAW and 3D-PSSM. *Proteins Suppl* 5: 39-46.

Blechman J M, Lev S, Barg J, Eisenstein M, Vaks B, Vogel Z, Givol D, Yarden Y. 1995. The fourth immunoglobulin domain of the stem cell factor receptor couples ligand binding to signal transduction. *Cell* 80(1): 103-113.

Bonifer C, Hume D A. 2008. The transcriptional regulation of the Colony-Stimulating Factor 1 Receptor (csf1r) gene during hematopoiesis. *Front Biosci* 13: 549-560.

Chen X, Liu H, Focia P J, Shim A H, He X. 2008. Structure of macrophage colony stimulating factor bound to FMS: diverse signaling assemblies of class III receptor tyrosine kinases. *Proc Natl Acad Sci USA* 105(47): 18267-18272.

Chitu V, Stanley E R. 2006. Colony-stimulating factor-1 in immunity and inflammation. *Curr Opin immunol* 18(1): 39-48.

Contreras-Moreira B, Bates P A. 2002. Domain fishing: a first step in protein comparative modelling. *Bioinformatics* 18(8): 1141-1142.

Dai X M, Ryan G R, Hapel A J, Dominguez M G, Russell R G, Kapp S, Sylvestre V, Stanley E R. 2002. Targeted disruption of the mouse colony-stimulating factor 1 receptor gene results in osteopetrosis, mononuclear phagocyte deficiency, increased primitive progenitor cell frequencies, and reproductive defects. *Blood* 99(1): 111-120.

Dai X M, Zong X H, Sylvestre V, Stanley E R. 2004. Incomplete restoration of colony-stimulating factor 1 (CSF-1) function in CSF-1-deficient Csflop/Csflop mice by transgenic expression of cell surface CSF-1. *Blood* 103(3): 1114-1123.

Fares M A, McNally D. 2006a. CAPS: coevolution analysis using protein sequences. *Bioinformatics* 22(22): 2821-2822.

-.2006b. CAPS: coevolution analysis using protein sequences. *Bioinformatics* 22(22): 2821-2822.

Fares M A, Travers S A. 2006a. A novel method for detecting intramolecular coevolution: adding a further dimension to selective constraints analyses. *Genetics* 173(1): 9-23.

Fares M A, Travers S A A. 2006b. A novel method for detecting intramolecular coevolution: Adding a further dimension to selective constraints analyses. *Genetics* 173(1): 9-23.

Faust N, Bonifer C, Sippel A E. 1999. Differential activity of the −2.7 kb chicken lysozyme enhancer in macrophages of different ontogenic origins is regulated by C/EBP and PU.1 transcription factors. *DNA Cell Biol* 18(8): 631-642.

Francey T, Schalch L, Brcic M, Peterhans E, Jungi T W. 1992. Generation and functional characterization of ovine bone marrow-derived macrophages. *Veterinary immunology and immunopathology* 32(3-4): 281-301.

Fuchs A, Martin-Galiano A J, Kalman M, Fleishman S, Ben-Tal N, Frishman D. 2007. Co-evolving residues in membrane proteins. *Bioinformatics* 23: 3312-3319.

Gibson M S, Kaiser P, Fife M. 2009. Identification of chicken granulocyte colony-stimulating factor (G-CSF/CSF3): the previously described myelomonocytic growth factor is actually CSF3. *J Interferon Cytokine Res* 29(6): 339-343.

Guilbert L J, Stanley E R. 1986. The interaction of 125I-colony-stimulating factor-1 with bone marrow-derived macrophages. *J Biol Chem* 261(9): 4024-4032.

Hamburger V, Hamilton H L, 1992. A series of normal stages in the development of the chick embryo. 1951. *Dev Dyn* 195(4): 231-272.

Hanington P C, Wang T, Secombes C J, Belosevic M. 2007. Growth factors of lower vertebrates: characterization of goldfish (*Carassius auratus* L.) macrophage colony-stimulating factor-1. *J Biol Chem* 282(44): 31865-31872.

Henikoff S, Henikoff J G. 1992. Amino acid substitution matrices from protein blocks. *Proceedings of the National Academy of Sciences of the United States of America* 89(22): 10915-10919.

Himes S R, Cronau S, Mulford C, Hume D A. 2005. The Runx1 transcription factor controls CSF-1-dependent and -independent growth and survival of macrophages. *Oncogene* 24(34): 5278-5286.

Himes S R, Tagoh H, Goonetilleke N, Sasmono T, Oceandy D, Clark R, Bonifer C, Hume D A. 2001. A highly conserved c-fms gene intronic element controls macrophage-specific and regulated expression. *J Leukoc Biol* 70(5): 812-820.

Hume D A, Ross I L, Himes S R, Sasmono R T, Wells C A, Ravasi T. 2002. The mononuclear phagocyte system revisited. *J Leukoc Biol* 72(4): 621-627.

Irvine K M, Burns C J, Wilks A F, Su S, Hume D A, Sweet M J. 2006. A CSF-1 receptor kinase inhibitor targets effector functions and inhibits pro-inflammatory cytokine production from murine macrophage populations. *FASEB J* 20(11): 1921-1923.

Jang M H, Herber D M, Jiang X, Nandi S, Dai X M, Zeller G, Stanley E R, Kelley V R. 2006. Distinct in vivo roles of colony-stimulating factor-1 isoforms in renal inflammation. *J Immunol* 177(6): 4055-4063.

Jiang X, Gurel O, Mendiaz E A, Stearns G W, Clogston C L, Lu H S, Osslund T D, Syed R S, Langley K E, Hendrickson W A. 2000. Structure of the active core of human stem cell factor and analysis of binding to its receptor kit. *EMBO J* 19(13): 3192-3203.

Jones D T. 1999. Protein secondary structure prediction based on position-specific scoring matrices. *J Mol Biol* 292(2): 195-202.

Kaiser P. 2007. The avian immune genome—a glass half-full or half-empty? *Cytogenetic and genome research* 117(1-4): 221-230.

Koths K. 1997. Structure-function studies on human macrophage colony-stimulating factor (M-CSF). *Mol Reprod Dev* 46(1): 31-37; discussion 37-38.

Lemmon M A, Pinchasi D, Zhou M, Lax I, Schlessinger J. 1997. Kit receptor dimerization is driven by bivalent binding of stem cell factor. *J Biol Chem* 272(10): 6311-6317.

Lichanska A M, Browne C M, Henkel G W, Murphy K M, Ostrowski M C, McKercher S R, Maki R A, Hume D A. 1999. Differentiation of the mononuclear phagocyte system during mouse embryogenesis: the role of transcription factor PU.1. *Blood* 94(1): 127-138.

Lichanska A M, Hume D A. 2000. Origins and functions of phagocytes in the embryo. *Exp Hematol* 28(6): 601-611.

Lin H, Lee E, Hestir K, Leo C, Huang M, Bosch E, Halenbeck R, Wu G, Zhou A, Behrens D et al., 2008. Discovery of a cytokine and its receptor by functional screening of the extracellular proteome. *Science* 320(5877): 807-811.

Marks S C, Jr., Wojtowicz A, Szperl M, Urbanowska E, MacKay C A, Wiktor-Jedrzejczak W, Stanley E R, Aukerman S L. 1992. Administration of colony stimulating factor-1 corrects some macrophage, dental, and skeletal defects in an osteopetrotic mutation (toothless, tl) in the rat. *Bone* 13(1): 89-93.

Nandi S, Akhter M P, Seifert M F, Dai X M, Stanley E R. 2006. Developmental and functional significance of the CSF-1 proteoglycan chondroitin sulfate chain. *Blood* 107(2): 786-795.

Nieto M A, Patel K, Wilkinson D G. 1996. In situ hybridization analysis of chick embryos in whole mount and tissue sections. *Methods Cell Biol* 51: 219-235.

Pandit J, Bohm A, Jancarik J, Halenbeck R, Koths K, Kim S H. 1992. Three-dimensional structure of dimeric human recombinant macrophage colony-stimulating factor. *Science* 258(5086): 1358-1362.

Park D J. 2004. 3' RACE LaNe: a simple and rapid fully nested PCR method to determine 3'-terminal cDNA sequence. *Biotechniques* 36(4): 586-588, 590.

Pollard J W. 1997. Role of colony-stimulating factor-1 in reproduction and development. *Mol Reprod Dev* 46(1): 54-60; discussion 60-51.

-.2009. Trophic macrophages in development and disease. *Nat Rev Immunol* 9(4): 259-270.

Porollo A, Meller J. 2007. Versatile annotation and publication quality visualization of protein complexes using POLYVIEW-3D. *BMC bioinformatics* 8: 316.

Rae F, Woods K, Sasmono T, Campanale N, Taylor D, Ovchinnikov D A, Grimmond S M, Hume D A, Ricardo S D, Little M H. 2007. Characterisation and trophic functions of murine embryonic macrophages based upon the use of a Csflr-EGFP transgene reporter. *Dev Biol* 308(1): 232-246.

Ramsoondar J, Christopherson R J, Guilbert L J, Wegmann T G. 1993. A porcine trophoblast cell line that secretes growth factors which stimulate porcine macrophages. *Biol Reprod* 49(4): 681-694.

Reddy M A, Yang B S, Yue X, Barnett O, Ross I L, Sweet M J, Hume D A, Ostrowski M C. 1994. Opposing actions of c-ets/PU.1 and c-myb protooncogene products in regulating the macrophage-specific promoters of the human and mouse colony-stimulating factor-1 receptor (c-fms) genes. *J Exp Med* 180(6): 2309-2319.

Rosnet O, Birnbaum D. 1993. Hematopoietic receptors of class III receptor-type tyrosine kinases. *Crit Rev Oncog* 4(6): 595-613.

Rovida E, Paccagnini A, Del Rosso M, Peschon J, Dello Sbarba P. 2001. TNF-alpha-converting enzyme cleaves the macrophage colony-stimulating factor receptor in macrophages undergoing activation. *J Immunol* 166(3): 1583-1589.

Rowlinson S W, Yoshizato H, Barclay J L, Brooks A J, Behncken S N, Kerr L M, Millard K, Palethorpe K, Nielsen K, Clyde-Smith J et al. 2008. An agonist-induced conformational change in the growth hormone receptor determines the choice of signalling pathway, *Nat Cell Biol* 10(6): 740-747.

Ryan G R, Dai X M, Dominguez M G, Tong W, Chuan F, Chisholm O, Russell R G, Pollard J W, Stanley E R, 2001. Rescue of the colony-stimulating factor 1 (CSF-1)-nullizygous mouse (Csfl(op)/Csfl(op)) phenotype with a CSF-1 transgene and identification of sites of local CSF-1 synthesis. *Blood* 98(1): 74-84.

Sasmono R T, Oceandy D, Pollard J W, Tong W, Pavli P, Wainwright B J, Ostrowski M C, Himes S R, Hume D A. 2003. A macrophage colony-stimulating factor receptor-green fluorescent protein transgene is expressed throughout the mononuclear phagocyte system of the mouse. *Blood* 101(3): 1155-1163.

Sester D P, Beasley S J, Sweet M J, Fowles L F, Cronau S L, Stacey K J, Hume D A. 1999. Bacterial/CpG DNA downmodulates colony stimulating factor-1 receptor surface expression on murine bone marrow-derived macrophages with concomitant growth arrest and factor-independent survival. *J Immunol* 163(12): 6541-6550.

Shannon P, Markiel A, Ozier O, Baliga N S, Wang J T, Ramage D, Amin N, Schwikowski B, Ideker T. 2003. Cytoscape: A software environment for integrated models of biomolecular interaction networks. *Genome Research* 13(11): 2498-2504.

Stanley E R, Guilbert L J. 1981. Methods for the purification, assay, characterization and target cell binding of a colony stimulating factor (CSF-1). *J Immunol Methods* 42(3): 253-284.

Strockbine L D, Cohen J I, Farrah T, Lyman S D, Wagener F, DuBose R F, Armitage R J, Spriggs M K. 1998. The Epstein-Barr virus BARF1 gene encodes a novel, soluble colony-stimulating factor-1 receptor. *J Virol* 72(5): 4015-4021.

Sweet M J, Hume D A. 2003. CSF-1 as a regulator of macrophage activation and immune responses. *Arch Immunol Ther Exp (Warsz)* 51(3): 169-177.

Tagoh H, Himes R, Clarke D, Leenen P J, Riggs A D, Hume D, Bonifer C. 2002. Transcription factor complex formation and chromatin fine structure alterations at the murine c-fms (CSF-1 receptor) locus during maturation of myeloid precursor cells. *Genes Dev* 16(13): 1721-1737.

Tamura T, Hadwiger-Fangmeier A. Boschek B. Niemann H. 1990. Transformation of chicken fibroblasts by the v-fms oncogene. *Virology* 178(2): 401-409.

Tamura T, Hadwiger-Fangmeier A, Simon E, Smola U, Geschwill H, Schutz B, Trouliaris S, Boscheck B, Niemann H, Bauer H. 1991. Transforming mechanism of the feline sarcoma virus encoded v-fms oncogene product. *Behring Inst Mitt* (89): 93-99.

Taylor E W, Fear A L, Bohm A, Kim S H, Koths K. 1994. Structure-function studies on recombinant human macrophage colony-stimulating factor (M-CSF). *J Biol Chem* 269(49): 31171-31177.

Thompson J D, Higgins D G, Gibson T J. 1994. CLUSTAL W: improving the sensitivity of progressive multiple sequence alignment through sequence weighting, position-specific gap penalties and weight matrix choice. *Nucleic acids research* 22(22): 4673-4680.

Tomlinson M L, Garcia-Morales C, Abu-Elmagd M, Wheeler G N. 2008. Three matrix metalloproteinases are required in vivo for macrophage migration during embryonic development. *Mech Dev* 125(11-12): 1059-1070.

Travers S A A, Fares M A. 2007. Functional coevolutionary networks of the Hsp70-Hop-Hsp90 system revealed through computational analyses. *Molecular Biology and Evolution* 24(4): 1032-1044.

Travers S A A, Tully D C, McCormack G P, Fares M A. 2007. A study of the coevolutionary patterns operating within the env gene of the HIV-1 group M subtypes. *Molecular Biology and Evolution* 24(12): 2787-2801.

Wang T, Hanington P C, Belosevic M, Secombes C J. 2008. Two macrophage colony-stimulating factor genes exist in fish that differ in gene organization and are differentially expressed. *J Immunol* 181(5): 3310-3322.

Westfall P H, Young S S. 1993. *Resampling-based multiple testing*. New York: John Wiley and Sons.

Woolford J, McAuliffe A, Rohrschneider L R. 1988. Activation of the feline c-fms proto-oncogene: multiple alterations are required to generate a fully transformed phenotype. *Cell* 55(6): 965-977.

Yoshihara K, Inumaru S, Hirota Y, Momotani E. 1998. Cloning and sequencing of cDNA encoding bovine macrophage colony-stimulating factor (bM-CSF) and expression of recombinant bM-CSF using baculovirus. *Veterinary immunology and immunopathology* (4): 381-391.

---

The invention claimed is:

1. An isolated DNA comprising a cDNA that comprises the nucleotide sequence of SEQ ID NO:1, 2, or 4.

2. An isolated DNA comprising a cDNA that encodes the amino acid sequence of SEQ NO:3 or 5.

3. The isolated DNA of claim 1, wherein the cDNA encodes an avian colony stimulating factor 1 (CSF1) protein.

4. An expression vector comprising a DNA sequence;
   wherein the DNA sequence comprises the nucleotide sequence of SEQ ID NO:1, 2, or 4.

5. An expression vector comprising a DNA sequence encoding the amino acid sequence of SEQ ID NO:3 or 5.

6. An isolated host cell transformed with the expression vector of claim 4.

7. An isolated host cell transformed with the expression vector of claim 5.

* * * * *

SEQUENCE LISTING

```
<160> NUMBER OF SEQ ID NOS: 10

<210> SEQ ID NO 1
<211> LENGTH: 2711
<212> TYPE: DNA
<213> ORGANISM: Gallus gallus

<400> SEQUENCE: 1
ataaagggca gcgcggcggc gacggcggac tcagcccggc cccgctccgc cgccttctcc      60
cgcaccgccc gacccgccgc agcccggcc ccacggcagc ccccatgccc cgcctcggat     120
```

```
cccaggtgtc cctgttccgc tgcaccctgc tctcgtccct cctcctcgtc tgcagcatcc    180
atgagacgga gcagaacagc tactgccagc agatcatcac cgagcggcac ctggaccacc    240
tgcaggagct ggcggacacg cagatgcagc agccgggcac agtgtccttc agattcatca    300
gcaagatgcg gctgagcgac tctgtctgct acgtgaaagc cgccttccct ttgctgggca    360
ccatcctgaa caggacgacg ttcaaggaga actcaacaaa cgccaacaag atgaagacgg    420
tgcgcaagat gtacgaaaac atcgatgaga cgtggaccc ctgcatcagg gacgaggatg     480
acaaggagca cgcgctgtcc gaaatgtgct ttgaggagtt caccacgtcc ccctacgaga    540
tgctggtgct ggtgaggcag ttcttccagg acatcaaaca gctgctgcag aacaaggaga    600
ccttcgagaa ggactgcagc caggtgtacc gcagtgcgtg cgcggggccc cggcagcaca    660
gctcctcccc aggtgtgggg acagatcctg actgcaattg cctgtcccct gcctcccctt    720
ctgccaccca gccctccctc tccgctgcca cccgtgccgg cagggacgtg gcgcccgcta    780
gcaccagggt cccttaccgc cagctcgtg gcatcctggc tgagttaggc agcagtgccc     840
cgtccgagcc ccccagtagc gtggagggca gctcgggggc cgaggaactg ccaggagccg    900
ggctcggcga cgcgtcggcg ccgtcccca ccatgcagca gacgcttgga gccctcctgg     960
atccagccgc gagcgccggc ccgaaggctg aggacgtatc catcccgtcc cacgggatgc   1020
cggaggaggg cgccgggacc cccgcccctcc cacatcggct cccttcgccg cgagggatca   1080
gcgcggcgat gccggcggcg gtcccccagca gcggctctgc gcagcgccgc ggggtcgggc   1140
gccgtcccac cgagagcccc gagcgggtca cgcagctccg cttccccagg atggctccgc   1200
cgttgcgggg ccgggcggag ggcggccccg gggacggggc gagggcgcga ggctgggggc   1260
tgagccggct gcgggagccc gaggacgcgc gggccggacc cagctttgat tcgagctttg   1320
ttctgagcgc agagcagcgc aggaaggagc cgccagccgc cagcggggg caccgggagc    1380 tcctggtgta cgtcacggtg gccagctgg tggccgtgct gctggccatg ggcgggctgc    1440
tcttctacaa gtataagtcc aaggtcctgc agcggggagc agcgctaaaa gagggggct    1500 gcgaccccga ggagccggag agcagggcgc tgcaggagc gcaggctgc gcggagctgg     1560 agacgcagga gctgtgaggg cccctgcgg gacgtgatgc tgctcggggg gacggacggg    1620
gacgctcctc gctgggcgac ggacggctgc tgctcggcct cccccgccg cgatgacccc    1680 caggccctgt cctgcagctg caacccacg gtgaggatgg caggacgggg cggtgcagcc    1740
ctgcaggacc ccggcgatgg ggcggatggc accgaggggc tccacgggga cggcattggg   1800
tgccgcgagt ggaacatctc ccccaccca tccacggttc ccgttgctcc tctcccaccc    1860
ctggcacggg gggaccccg gcgcccatg ggggacccc tcccgcatcc caccggtgcc      1920
gaggacccaa cgcccggcct gcaaaggggg aaaccctcac actgtgaata tttaagaccc    1980
gtggtgccgt cccatcccg cgatcccaag ctggccttgg gagctgcccg gcgccgctct    2040
gcgcaggaag gctctccacg aacgcggtgg ataaacgctt ttatccaaca aatgcacttg    2100 ggggggggg ttcccccctc cctgcagggt tattgctgcg agctggcctc gccccagact    2160
ggattttgtt gctggagcac agcacggcaa tggggccgtg gctgcagtgt ggggtttggg   2220
ggctcagcgg taccccggact gcgtcccacc ccacacggca tccctgccca cgccgctcc    2280 cggggggtcg gaagtgttat ttttatatta catgagatgc aaacgggacg gagcacattg    2340
gggtgtggtg gggttttgtt ttttaaagca ttagtattga ttttgggtt ttttttcta     2400 tgcgtattta tggactgcca aaaaagagg cgtttcctgg gggtgatggg ggggggggtg    2460
```

-continued

| | |
|---|---|
| gaagtggggt gcagagccgg gctggggccg gagctggtgc tggctcagta tgtgggtgt | 2520 |
| gggtgagggg ggttgggggg ggggcagctt ttggagctct ttctgcctct gttgtctcat | 2580 |
| tttttgtaca gtgaaatggt gaaatatttt atacaaagtc atttaaagaa gtctatttaa | 2640 |
| ggaaaataat agaaaacagc ttgtatattt aatattatta ataaagatgg acgtgcaaaa | 2700 |
| aaaaaaaaaa a | 2711 |

<210> SEQ ID NO 2
<211> LENGTH: 1473
<212> TYPE: DNA
<213> ORGANISM: Gallus gallus

<400> SEQUENCE: 2

| | |
|---|---|
| atgccccgcc tcggatccca ggtgtccctg ttccgctgca ccctgctctc gtccctcctc | 60 |
| ctcgtctgca gcatccatga gacggagcag aacagctact gccagcagat catcaccgag | 120 |
| cggcacctgg accacctgca ggagctggcg gacacgcaga tgcagcagcc gggcacagtg | 180 |
| tccttcagat tcatcagcaa gatgcggctg agcgactctg tctgctacgt gaaagccgcc | 240 |
| ttccctttgc tggcaccat cctgaacagg acgacgttca aggagaactc aacaaacgcc | 300 |
| aacaagatga agacggtgcg caagatgtac gaaaacatcg atgagaacgt ggaccctgc | 360 |
| atcagggacg aggatgacaa ggagcacgcg ctgtccgaaa tgtgctttga ggagttcacc | 420 |
| acgtccccct acgagatgct ggtgctggtg aggcagttct ccaggacat caaacagctg | 480 |
| ctgcagaaca aggagacctt cgagaaggac tgcagccagg tgtaccgcag tgcgtgcgcg | 540 |
| gggccccggc agcacagctc ctccccaggt gtggggacag atcctgactg caattgcctg | 600 |
| tcccctgccc tccttctgc cacccagccc tccctctccg ctgccacccg tgccggcagg | 660 |
| gacgtggcgc ccgctagcac cagggtccct taccgccagc tcgtggcat cctggctgag | 720 |
| ttaggcagca gtgccccgtc cgagccccc agtagcgtgg agggcagctc gggggccgag | 780 |
| gaactgccag gagccgggct cggcgacgcg tcggcgccgt cccccaccat gcagcagacg | 840 |
| cttggagccc tcctggatcc agccgcgagc gccggcccga aggctgagga cgtatccatc | 900 |
| ccgtcccacg ggatgccgga ggagggcgcc gggaccccg ccctcccaca tcggctccct | 960 |
| tcgccgcgag ggatcagcgc ggcgatgccg gcggcggtcc ccagcagcgg ctctgcgcag | 1020 |
| cgccgcgggg tcgggcgccg tcccaccgag agccccgagc gggtcacgca gctccgcttc | 1080 |
| cccaggatgg ctccgccgtt gcggggccgg gcggagggcg gccccgggga cggggcgagg | 1140 |
| gcgcgaggct gggggctgag ccggctgcgg gagcccgagg acggcggggc cggacccagc | 1200 |
| tttgattcga gctttgttct gagcgcagag cagcgcagga aggagccgcc agccgccagc | 1260 |
| gggggggcacc gggagctcct ggtgtacgtc acggtggcca gcgtggtggc cgtgctgctg | 1320 |
| gccatgggcg ggctgctctt ctacaagtat aagtccaagg tcctgcagcg gggagcagcg | 1380 |
| ctaaaagagg ggggctgcga cccccgaggag ccggagagca gggcgctgca gggagcgcag | 1440 |
| ggctgcgcgg agctggagac gcaggagctg tga | 1473 |

<210> SEQ ID NO 3
<211> LENGTH: 490
<212> TYPE: PRT
<213> ORGANISM: Gallus gallus

<400> SEQUENCE: 3

Met Pro Arg Leu Gly Ser Gln Val Ser Leu Phe Arg Cys Thr Leu Leu
1               5                   10                  15

-continued

```
Ser Ser Leu Leu Leu Val Cys Ser Ile His Glu Thr Glu Gln Asn Ser
             20                  25                  30

Tyr Cys Gln Gln Ile Ile Thr Glu Arg His Leu Asp His Leu Gln Glu
         35                  40                  45

Leu Ala Asp Thr Gln Met Gln Gln Pro Gly Thr Val Ser Phe Arg Phe
     50                  55                  60

Ile Ser Lys Met Arg Leu Ser Asp Ser Val Cys Tyr Val Lys Ala Ala
65                  70                  75                  80

Phe Pro Leu Leu Gly Thr Ile Leu Asn Arg Thr Thr Phe Lys Glu Asn
                 85                  90                  95

Ser Thr Asn Ala Asn Lys Met Lys Thr Val Arg Lys Met Tyr Glu Asn
             100                 105                 110

Ile Asp Glu Asn Val Asp Pro Cys Ile Arg Asp Glu Asp Lys Glu
         115                 120                 125

His Ala Leu Ser Glu Met Cys Phe Glu Glu Phe Thr Thr Ser Pro Tyr
     130                 135                 140

Glu Met Leu Val Leu Val Arg Gln Phe Phe Gln Asp Ile Lys Gln Leu
145                 150                 155                 160

Leu Gln Asn Lys Glu Thr Phe Glu Lys Asp Cys Ser Gln Val Tyr Arg
                 165                 170                 175

Ser Ala Cys Ala Gly Pro Arg Gln His Ser Ser Pro Gly Val Gly
             180                 185                 190

Thr Asp Pro Asp Cys Asn Cys Leu Ser Pro Ala Leu Pro Ser Ala Thr
         195                 200                 205

Gln Pro Ser Leu Ser Ala Ala Thr Arg Ala Gly Arg Asp Val Ala Pro
     210                 215                 220

Ala Ser Thr Arg Val Pro Tyr Arg Gln Leu Gly Gly Ile Leu Ala Glu
225                 230                 235                 240

Leu Gly Ser Ser Ala Pro Ser Glu Pro Pro Ser Ser Val Glu Gly Ser
                 245                 250                 255

Ser Gly Ala Glu Glu Leu Pro Gly Ala Gly Leu Gly Asp Ala Ser Ala
             260                 265                 270

Pro Ser Pro Thr Met Gln Gln Thr Leu Gly Ala Leu Leu Asp Pro Ala
         275                 280                 285

Ala Ser Ala Gly Pro Lys Ala Glu Asp Val Ser Ile Pro Ser His Gly
     290                 295                 300

Met Pro Glu Glu Gly Ala Gly Thr Pro Ala Leu Pro His Arg Leu Pro
305                 310                 315                 320

Ser Pro Arg Gly Ile Ser Ala Met Pro Ala Ala Val Pro Ser Ser
                 325                 330                 335

Gly Ser Ala Gln Arg Arg Gly Val Gly Arg Arg Pro Thr Glu Ser Pro
             340                 345                 350

Glu Arg Val Thr Gln Leu Arg Phe Pro Arg Met Ala Pro Pro Leu Arg
         355                 360                 365

Gly Arg Ala Glu Gly Gly Pro Gly Asp Gly Ala Arg Ala Arg Gly Trp
     370                 375                 380

Gly Leu Ser Arg Leu Arg Glu Pro Glu Asp Gly Gly Ala Gly Pro Ser
385                 390                 395                 400

Phe Asp Ser Ser Phe Val Leu Ser Ala Glu Gln Arg Arg Lys Glu Pro
                 405                 410                 415

Pro Ala Ala Ser Gly Gly His Arg Glu Leu Leu Val Tyr Val Thr Val
             420                 425                 430

Ala Ser Val Val Ala Val Leu Leu Ala Met Gly Gly Leu Leu Phe Tyr
```

```
                435                440                445
Lys Tyr Lys Ser Lys Val Leu Gln Arg Gly Ala Ala Leu Lys Glu Gly
        450                455                460

Gly Cys Asp Pro Glu Glu Pro Glu Ser Arg Ala Leu Gln Gly Ala Gln
465                470                475                480

Gly Cys Ala Glu Leu Glu Thr Gln Glu Leu
                485                490

<210> SEQ ID NO 4
<211> LENGTH: 813
<212> TYPE: DNA
<213> ORGANISM: Gallus gallus

<400> SEQUENCE: 4
atgccccgcc tcggatccca ggtgtccctg ttccgctgca ccctgctctc gtccctcctc      60
ctcgtctgca gcatccatga cggagcag aacagctact gccagcagat catcaccgag      120
cggcacctgg accacctgca ggagctggcg gacacgcaga tgcagcagcc gggcacagtg      180
tccttcagat tcatcagcaa gatgcggctg agcgactctg tctgctacgt gaaagccgcc      240 ttcccctttgc tgggcaccat cctgaacagg acgacgttca aggagaactc aacaaacgcc      300
aacaagatga agacggtgcg caagatgtac gaaaacatcg atgaggacgt ggacccctgc      360
atcagggacg aggatgacga ggagcacgcg ctgtccgaaa tgtgctttga ggagttcacc      420
acgtccccct acgagatgct ggtgctggtg aggcagttct tccaggacat caaacagctg      480
ctgcagaaca aggagacctt cgagaaggac tgcagccagg tgtaccgcag tgcgtgcgcg      540
gggccccggc agcacagctc ctccccagag cagcgcagga aggagccgcc agccgccagc      600 gggggggcacc gggagctcct ggtgtacgtc acggtggcca gcgtggtggc cgtgctgctg      660
gccatgggcg gctgctcttt ctacaagtat aagtccaagg tcctgcagcg gggagcagcg      720
ctaaaagagg ggggctgcga ccccgaggag ccggagagca gggcgctgca gggagcgcag      780
ggctgcgcgg agctggagac gcaggagctg tga                                  813

<210> SEQ ID NO 5
<211> LENGTH: 270
<212> TYPE: PRT
<213> ORGANISM: Gallus gallus

<400> SEQUENCE: 5

Met Pro Arg Leu Gly Ser Gln Val Ser Leu Phe Arg Cys Thr Leu Leu
1               5                   10                  15

Ser Ser Leu Leu Leu Val Cys Ser Ile His Glu Thr Glu Gln Asn Ser
            20                  25                  30

Tyr Cys Gln Gln Ile Ile Thr Glu Arg His Leu Asp His Leu Gln Glu
        35                  40                  45

Leu Ala Asp Thr Gln Met Gln Gln Pro Gly Thr Val Ser Phe Arg Phe
    50                  55                  60

Ile Ser Lys Met Arg Leu Ser Asp Ser Val Cys Tyr Val Lys Ala Ala
65                  70                  75                  80

Phe Pro Leu Leu Gly Thr Ile Leu Asn Arg Thr Thr Phe Lys Glu Asn
                85                  90                  95

Ser Thr Asn Ala Asn Lys Met Lys Thr Val Arg Lys Met Tyr Glu Asn
            100                 105                 110

Ile Asp Glu Asp Val Asp Pro Cys Ile Arg Asp Glu Asp Asp Glu Glu
        115                 120                 125
```

His Ala Leu Ser Glu Met Cys Phe Glu Glu Phe Thr Thr Ser Pro Tyr
            130                 135                 140

Glu Met Leu Val Leu Val Arg Gln Phe Phe Gln Asp Ile Lys Gln Leu
145                 150                 155                 160

Leu Gln Asn Lys Glu Thr Phe Glu Lys Asp Cys Ser Gln Val Tyr Arg
                165                 170                 175

Ser Ala Cys Ala Gly Pro Arg Gln His Ser Ser Pro Glu Gln Arg
            180                 185                 190

Arg Lys Glu Pro Pro Ala Ala Ser Gly Gly His Arg Glu Leu Leu Val
                195                 200                 205

Tyr Val Thr Val Ala Ser Val Val Ala Val Leu Leu Ala Met Gly Gly
            210                 215                 220

Leu Leu Phe Tyr Lys Tyr Lys Ser Lys Val Leu Gln Arg Gly Ala Ala
225                 230                 235                 240

Leu Lys Glu Gly Gly Cys Asp Pro Glu Glu Pro Glu Ser Arg Ala Leu
                245                 250                 255

Gln Gly Ala Gln Gly Cys Ala Glu Leu Glu Thr Gln Glu Leu
            260                 265                 270

<210> SEQ ID NO 6
<211> LENGTH: 534
<212> TYPE: DNA
<213> ORGANISM: Gallus gallus

<400> SEQUENCE: 6
atgcaccagg gctgcgcggc tgtcctctgt gtcctggccg tgctggggct ggaggtggct      60
gcgctggggg aatgcgagct cgcccgcctg ctgcaggaca agctgcggta tgagatgcgc     120
ctgcagtaca tgaagcacaa cttccccatt gactacactc tccgggtgca gcacgaggag     180
gtgctgcgga ccgccaacgt caccgcctg cgtgatggga aggtgtcgga ggcgtcgctg      240
cgctacctgt ggttccacgc tgctcccag gcggtgctgc acatcctcga ggtgctgccg     300
gagaagcacc cgtcccgtgg gtacacgcag gagctgagcc agcttttgga tgccctgggc     360
gtggagtaca gtgggtaccg gcagagcgat gtggacgcgg tggtggccga cctggtgaag     420
cagctgcaca gcggcgatag ccggcagaag gccgtgcgcc ccaaagcact gctgacaac      480 tgcctcaagg tcctgcggat gctcttcggg gcacactgtc ggtgggactc cgct          534

<210> SEQ ID NO 7
<211> LENGTH: 178
<212> TYPE: PRT
<213> ORGANISM: Gallus gallus

<400> SEQUENCE: 7

Met His Gln Gly Cys Ala Ala Val Leu Cys Val Leu Ala Val Leu Gly
1               5                   10                  15

Leu Glu Val Ala Ala Leu Gly Glu Cys Glu Leu Ala Arg Leu Leu Gln
                20                  25                  30

Asp Lys Leu Arg Tyr Glu Met Arg Leu Gln Tyr Met Lys His Asn Phe
            35                  40                  45

Pro Ile Asp Tyr Thr Leu Arg Val Gln His Glu Glu Val Leu Arg Thr
        50                  55                  60

Ala Asn Val Thr Arg Leu Arg Asp Gly Lys Val Ser Glu Ala Ser Leu
65                  70                  75                  80

Arg Tyr Leu Trp Phe His Ala Cys Ser Gln Ala Val Leu His Ile Leu
                85                  90                  95

```
Glu Val Leu Pro Glu Lys His Pro Ser Arg Gly Tyr Thr Gln Leu
            100                 105                 110
Ser Gln Leu Leu Asp Ala Leu Gly Val Glu Tyr Ser Gly Tyr Arg Gln
    115                 120                 125
Ser Asp Val Asp Ala Val Val Ala Asp Leu Val Lys Gln Leu His Ser
130                 135                 140
Gly Asp Ser Arg Gln Lys Ala Val Arg Pro Lys Ala Leu Leu Asp Asn
145                 150                 155                 160
Cys Leu Lys Val Leu Arg Met Leu Phe Gly Ala His Cys Arg Trp Asp
                165                 170                 175
Ser Ala
```

<210> SEQ ID NO 8
<211> LENGTH: 20
<212> TYPE: DNA
<213> ORGANISM: Artificial
<220> FEATURE:
<223> OTHER INFORMATION: Primer

<400> SEQUENCE: 8
gcgactctgt ctgctacgtg                                            20

<210> SEQ ID NO 9
<211> LENGTH: 20
<212> TYPE: DNA
<213> ORGANISM: Artificial
<220> FEATURE:
<223> OTHER INFORMATION: Primer

<400> SEQUENCE: 9
cgaaggtctc cttgttctgc                                            20

<210> SEQ ID NO 10
<211> LENGTH: 159
<212> TYPE: PRT
<213> ORGANISM: Gallus gallus

<400> SEQUENCE: 10

```
Asn Ser Tyr Cys Gln Gln Ile Ile Thr Glu Arg His Leu Asp His Leu
1               5                   10                  15
Gln Glu Leu Ala Asp Thr Gln Met Gln Gln Pro Gly Thr Val Ser Phe
            20                  25                  30
Arg Phe Ile Ser Lys Met Arg Leu Ser Asp Ser Val Cys Tyr Val Lys
        35                  40                  45
Ala Ala Phe Pro Leu Leu Gly Thr Ile Leu Asn Arg Thr Thr Phe Lys
    50                  55                  60
Glu Asn Ser Thr Asn Ala Asn Lys Met Lys Thr Val Arg Lys Met Tyr
65                  70                  75                  80
Glu Asn Ile Asp Glu Asn Val Asp Pro Cys Ile Arg Asp Glu Asp Asp
                85                  90                  95
Lys Glu His Ala Leu Ser Glu Met Cys Phe Glu Phe Thr Thr Ser
            100                 105                 110
Pro Tyr Glu Met Leu Val Leu Val Arg Gln Phe Phe Gln Asp Ile Lys
            115                 120                 125
Gln Leu Leu Gln Asn Lys Glu Thr Phe Glu Lys Asp Cys Ser Gln Val
    130                 135                 140
Tyr Arg Ser Ala Cys Ala Gly Pro Arg Gln His Ser Ser Ser Pro
145                 150                 155
```